US005976066A

United States Patent [19]
Yanch et al.

[11] Patent Number: 5,976,066
[45] Date of Patent: Nov. 2, 1999

[54] NEUTRON CAPTURE THERAPIES

[75] Inventors: Jacquelyn C. Yanch, Cambridge; Ruth E. Shefer, Newton; Robert E. Klinkowstein, Winchester, all of Mass.

[73] Assignees: Massachusetts Institute of Technology; Newton Scientific, Inc., both of Cambridge, Mass.

[21] Appl. No.: 08/919,870

[22] Filed: Aug. 28, 1997

Related U.S. Application Data

[60] Provisional application No. 60/025,092, Aug. 30, 1996.

[51] Int. Cl.$^6$ ...................................................... A61N 5/00
[52] U.S. Cl. ................................................................. 600/1
[58] Field of Search ........................... 600/1–8; 250/251; 604/20–21; 376/458, 194

[56] References Cited

U.S. PATENT DOCUMENTS

| | | |
|---|---|---|
| 4,675,150 | 6/1987 | Russell, Jr. et al. . |
| 5,011,797 | 4/1991 | Day et al. . |
| 5,039,326 | 8/1991 | Day et al. . |
| 5,392,319 | 2/1995 | Eggers ..................................... 376/194 |
| 5,433,693 | 7/1995 | Ott ............................................... 600/1 |
| 5,658,233 | 8/1997 | Peurrung ..................................... 600/1 |
| 5,703,918 | 12/1997 | Hiismaki et al. ....................... 376/458 |

OTHER PUBLICATIONS

Wollard et al., Proceeding of the First International Workshop on Accelerator–Based Neutron Sources for Boron Neutron Capture Therapy, "Optimization of a Moderator Assembly for use in an Accelerator–Based Epithermal Neutron Source for BNCT", vol. 1, pp. 327–338, Sep. 1994.

Zhou et al., Proceeding of the First International Workshop on Accelerator–Based Neutron Sources for Boron Neutron Capture Therapy, "Design of Neutron Beams at the Argonne Continuous Wave LINAC (ACWL) for Boron Neutron Capture Therapy and Neutron Radiography", vol. 1, pp. 427–440, Sep. 1994.

Hirota et al., Proceeding of the First International Workshop on Accelerator–Based Neutron Sources for Boron Neutron Capture Therapy, "Design Study of a Deuteron LINAC Facility for Boron Neutron Capture Therapy", vol. 1, pp. 389–400, Sep., 1994.

Kushin et al., Proceeding of the First International Workshop on Accelerator–Based Neutron Sources for Boron Neutron Capture Therapy, "Spectral and Dose Characterictics of Neutron Field Formed by Filter–Moderation for BNCT". vol. 1, pp. 279–290, Sep., 1994.

Binello et al., American Nuclear Society Radiation and Protection and Shielding Design Topical Meeting, "Monte Carlo Investigation of Optimal Neutron Beam Energy Required for Boron Neutron Capture Synovectomy", pp. 659–664, Apr. 1996.

Binello et al., Published in the Proceedings of the 7th International Symposium on Neutron Capture Therapy for Cancer, "Neutron Beam Design for Boron Neutron Capture Synovectomy", Sep., 1997.

(List continued on next page.)

*Primary Examiner*—Samuel Gilbert
*Attorney, Agent, or Firm*—Samuels, Gauthier & Stevens, LLP

[57] ABSTRACT

In one embodiment there is provided an application of the $^{10}B(n,\alpha)^7Li$ nuclear reaction or other neutron capture reactions for the treatment of rheumatoid arthritis. This application, called Boron Neutron Capture Synovectomy (BNCS), requires substantially altered demands on neutron beam design than for instance treatment of deep seated tumors. Considerations for neutron beam design for the treatment of arthritic joints via BNCS are provided for, and comparisons with the design requirements for Boron Neutron Capture Therapy (BNCT) of tumors are made. In addition, exemplary moderator/reflector assemblies are provided which produce intense, high-quality neutron beams based on (p,n) accelerator-based reactions. In another embodiment there is provided the use of deuteron-based charged particle reactions to be used as sources for epithermal or thermal neutron beams for neutron capture therapies. Many d,n reactions (e.g. using deuterium, tritium or beryllium targets) are very prolific at relatively low deuteron energies.

6 Claims, 23 Drawing Sheets

OTHER PUBLICATIONS

Agosteo et al., Proceeding of the First International Workshop on Accelerator–Based Neutron Sources for Boron Neutron Capture Therapy, "Monte Carlo Study of Thermal Neutron Source Generated by 11 MeV Protons and 7 MeV Deuterons", vol. 1, pp. 255–268, Sep., 1994.

Binello et al., Published in the Proceedings of the 7th International Symposium on Neutron Capture Therapy for Cancer, "In Vitro Analysis of $^{10}$B Uptake for Boron Neutron Capture Synovectomy", 1997.

Yanch et al., Med. Phys. "Accelerator–based epithermal neutron beam design for neutron capture therapy", vol. 19, No. 3, pp. 709–721, May/Jun. 1992.

| REACTION | ION ENERGY (MeV) | MAX. NEUTRON ENERGY (MeV) |
|---|---|---|
| $^7\text{Li}(p, n)^7\text{Be}$ | 2.5 | 0.8 |
| $^9\text{Be}(p, n)^9\text{B}$ | 4.0 | 2.1 |
| $^9\text{Be}(d, n)^{10}\text{B}$ | 2.6 – 7.0 | 7 – 11 |
| $t(d, n)^4\text{He}$ | 0.25 | 14 |
| $d(d, n)^3\text{He}$ | 0.25 | 2.5 |

*FIG. 2*

| TARGET:<br>D₂O LENGTH | SYNOVIUM DOSE-<br>TO-SKIN DOSE | SYNOVIUM DOSE-TO-<br>BONE SURFACE DOSE | THERAPY TIME<br>(min – mA) |
|---|---|---|---|
| Lithium: 20cm | 71 | 120 | 8 |
| Beryllium: 20cm | 43 | 73 | 15 |
| Lithium: 35cm | 171 | 213 | 27 |
| Beryllium: 35cm | 162 | 188 | 47 |
| Lithium: 50cm | 277 | 301 | 51 |
| Beryllium: 50cm | 236 | 281 | 69 |

*FIG. 12*

| MODERATOR/ REFLECTOR MATERIAL | SYNOVIUM DOSE - TO – SKIN DOSE | SYNOVIUM DOSE - TO – BONE DOSE | THERAPY TIME (min – mA) * |
|---|---|---|---|
| D$_2$O / LEAD | 42 | 47 | 49 |
| D$_2$O / GRAPHITE | 72 | 76 | 31 |
| D$_2$O / $^7$LiCO$_3$ | 66 | 66 | 48 |
| D$_2$O / D$_2$O | 75 | 76 | 44 |
| D$_2$O / AIR | 21 | 45 | 804 |
| GRAPHITE / GRAPHITE | 31 | 45 | 48 |

* using RBE values of 4.0 for $^{10}$B, 3.8 for neutrons and 1.0 for photons

** 1000 ppm of $^{10}$B modeled in the synovium

*FIG. 13*

| REACTION | ION ENERGY | MODERATOR LENGTH (cm) | SYNOVIUM/ SKIN RATIO | SYNOVIUM/ BONE RATIO | THERAPY TIME (min – mA) |
|---|---|---|---|---|---|
| $^7$Li (p, n) | 2.5 MeV | 20<br>35<br>50 | 71<br>171<br>277 | 120<br>213<br>301 | 8<br>27<br>51 |
| $^9$Be (p, n) | 4.0 MeV | 20<br>35<br>50 | 43<br>162<br>236 | 73<br>188<br>281 | 15<br>47<br>69 |
| $^9$Be (d, n) | 2.6 MeV | 20<br>30<br>50<br>50 | 24<br>50<br>61<br>32 | 33<br>57<br>74<br>41 | 8<br>17<br>100<br>7 |
| d (d, n) | 0.25 MeV | 30<br>50 | 13<br>36 | 19<br>46 | 2,316 *<br>4,540 * |
| t (d, n) | 0.25 MeV | 30<br>50 | 4<br>8 | 5<br>1 | 59 *<br>259 * |

\* Therapy times are for neutron fluxes obtainable from commercial neutron generators:
$4 \times 10^9$ n / sec for d (d, n) and $4 \times 10^{11}$ n / sec for t (d, n).

*FIG. 16*

| REFLECTOR MATERIAL | ADVANTAGE DEPTH (cm) | RBE DOSE RATE * at 1.5 cm (cGy / min – mA) | RBE DOSE RATE at 7 cm (cGy / min – mA) |
|---|---|---|---|
| LEAD | 8.6 | 17.3 | 5.7 |
| GRAPHITE | 6.8 | 10.2 | 2.5 |
| $Li_2CO_3$ | 6.0 | 7.0 | 2.0 |

*RBEs of 4.0, 3.8, and 1.0 used for $^{10}B(n, \alpha)$, neutrons and photons, respectively.

FIG. 22

NEUTRON CAPTURE THERAPIES

This application claims priority from provisional application Ser. No. 60/025,092 filed Aug. 30, 1996.

SPONSORSHIP INFORMATION

This invention was made with government support under Contract No. DE-FG02-89ER60874 awarded by the U.S. Department of Energy and under Grant No. R43AR43680 awarded by the NIH. The government has certain rights in the invention.

BACKGROUND OF THE INVENTION

Neutron capture therapies are two-part radiation therapies relying on the selective loading of tumor cells with a pharmaceutical containing $^{10}$B (or other isotopes with high neutron capture cross-sections) and subsequent tissue irradiation with thermal neutrons. Boron is nonradioactive until a thermal neutron is captured causing a $^{10}$B(n,$\alpha$)$^7$Li fission reaction. The resulting alpha and lithium particles are high in energy (sharing 2.3 MeV), LET, and RBE, and travel less than 10 microns in tissue. These features lead to selective tumor-cell killing provided the $^{10}$B-containing pharmaceutical localizes well in the tumor. Other nuclides with high neutron capture cross-sections could also be used.

An external beam of thermal neutrons will be able to treat $^{10}$B-loaded tumors located at, or close to, the tissue surface. However, thermal neutrons are attenuated very rapidly in tissue. The need to provide a high flux of thermal neutrons at greater depths can be realized if a neutron beam with higher than thermal energy is used. The abundance of light hydrogen in tissue allows the higher energy ("epithermal") neutrons to be moderated through elastic collisions.

As the energy of the external neutron beam is increased, the thermal neutron flux at a given depth is increased. However, if the energy of the epithermal neutron beam is too high, the skin sparing due to 1/v reduction in the capture cross-section of $^1$H and $^{14}$N (and any $^{10}$B located in healthy tissues near the surface) will be offset by an unacceptably large surface dose created by protons recoiling from collisions with fast neutrons. A trade-off must be realized, then, between maximizing the thermal neutron flux at depth, and minimizing the dose to healthy tissue (particularly at the surface). The question of which energy (or range of energies) results in the optimum trade-off for a particular neutron capture therapy application is important in the development of epithermal neutrons.

Sources of energetic neutrons include nuclear reactors and particle accelerators in which energetic charged particles bombard one or more of a variety of target materials. A number of reactions have been investigated as potential sources of epithermal neutrons including $^7$Li(p,n) at energies between 1.88 and 3.5 MeV, and $^9$Be(p,n) at energies between 1.8 and 4.1 MeV. These reactions are endothermic and require high power accelerators to generate sufficiently intense neutron beams. An alternate approach is to make use of the exothermic $^9$Be(d,n) reaction. This reaction generates large quantities of high energy neutrons unless the deuteron bombarding energy is set below 2.0 MeV. It is then possible to design spectrum shifters (moderator/reflector assemblies) such that the final epithermal neutron beam from the $^9$Be(d,n) reaction is suitable for clinical use in the treatment of deep-seated tumors (Boron Neutron Capture Therapy) or rheumatoid arthritis (Boron Neutron Capture Synovectomy).

Rheumatoid arthritis (RA) is a chronic autoimmune disease of the joints characterized by inflammation of the synovium, the membrane which lines the joint capsule. RA afflicts approximately 1% of the population of the United States and is three times as prevalent among women as men. Synovial inflammation is the primary cause of pain and physical disability in RA sufferers, with the most commonly affected joints being the knee (in 56% of the patients) and the metacarpophalangeal joints (in 87% of patients). If left untreated, chronic synovial inflammation eventually leads to the formation of pannus and the enzymatic destruction of the joint cartilage. Although the causes of cartilage destruction are not completely understood it is well established that the proliferation of inflamed synovium in the joint plays an important role.

The treatment of RA usually involves the use of various drug regimens aimed at reducing the synovial inflammation. While these therapies can satisfactorily control the symptoms of RA in a majority of patients, destruction of the joint still proceeds and eventually joint replacement becomes the only alternative.

Synovectomy, the removal or ablation of the inflamed membrane, has been shown to alleviate the symptoms of rheumatoid arthritis for periods of up to 5 years and may also slow the progress of cartilage and bone destruction. In surgical synovectomy, the membrane is excised either by open surgery or arthroscopy. These procedures have several serious drawbacks. First, the complex geometry of the joint space makes it virtually impossible to remove all the disease synovium. Second, the attendant dangers of surgery are always present, including infection and the risk of anesthesia. Finally, prolonged hospitalization and rehabilitation are often required, making this treatment both expensive and inconvenient for the patient.

Radiation synovectomy is presently the only alternative to surgical synovectomy. In radiation synovectomy, a beta-emitting radionuclide is injected directly into the joint space. Typically, the radionuclide is incorporated into a colloid which is rapidly taken up by the synovial lining through phagocytosis and delivers a lethal radiation dose (approximately 10,000 rad) to the synovium within a period of hours to weeks. Because the entire surface of the synovium is exposed to the radiopharmaceutical, there is a high likelihood of complete destruction of the diseased membrane. The synovium is typically several millimeters thick so beta-emitters which deposit their energy within 1–10 mm in tissue are used, including $^{198}$Au, $^{32}$P, $^{90}$Y, etc.

The efficacy of radiation synovectomy has been shown to be similar to that of surgical synovectomy, with reported success rates of up to 80% for the treatment of early-stage RA of the knee. Radiation synovectomy is much less invasive than surgical synovectomy: the radionuclide is usually administered in a single dose under local anesthetic and, in the case of the shorter-lived radionuclides such as $^{165}$Dy, no hospital stay is required. In addition, the required rehabilitation time is usually minimal. However, despite its many advantages over surgical synovectomy, radiation synovectomy has not gained acceptance in the United States because of the inherent dangers of internal radioisotope therapy.

The primary drawback of radiation synovectomy is the delivery of radiation dose to non-target organs due to leakage of the radionuclide-containing compound from the joint cavity. Investigators using colloids of $^{198}$Au and $^{90}$Y have reported leakage of a few percent up to as much as 60% of the injected dose. This is leakage has been shown to result in unacceptable radiation exposure to the liver, spleen, and lymphatic system.

SUMMARY OF THE INVENTION

The invention provides an application of the $^{10}$B(n,$\alpha$)$^7$Li nuclear reaction, or other neutron capture reactions, for the treatment of rheumatoid arthritis. This application, called Boron Neutron Capture Synovectomy (BNCS), requires substantially altered demands on neutron beam design than for instance treatment of deep seated tumors. Considerations for neutron beam design for the treatment of arthritic joints via BNCS are provided for, and comparisons with the design requirements for BNCT are made. In addition, exemplary moderator/reflector assemblies are provided which produce intense, high-quality neutron beams based on the $^7$Li(p,n) or the $^9$Be(p,n) accelerator-based reactions. Total therapy time and therapeutic ratios are given as a function of both moderator length and boron concentration. A means of carrying out multi-directional irradiations of arthritic joints is provided.

The invention also provides for the use of deuteron-based charged particle reactions to be used as sources for epithermal or thermal neutron beams for neutron capture therapies (for the treatment of cancer, arthritis and other diseases). Many d,n reactions (e.g. using deuteron, tritium or beryllium targets) are very prolific at relatively low deuteron energies. The advantage of high neutron yield however, is offset by the fact that these reactions have positive Q-values leading to the emission of high energy neutrons at even low particle bombarding energies. Using the Monte Carlo code MCNP (Monte Carlo for Neutron and Photon Transport), several (d,n) reactions were investigated in detail to determine their potential for generating clinically useful epithermal and thermal beams with sufficient intensity and low fast neutron contamination. Beam assessment was carried out both in air and in tissue equivalents of the brain and knee joint. Exemplary moderator/reflector assemblies are provided which produce intense, high-quality neutron beams based on the $^9$Be(d,n) accelerator-based reaction. Total therapy time and therapeutic ratios are given as a function of moderator length, beam energy and reflector material. A means of carrying out multi-directional irradiations of diseased tissue is provided.

BRIEF DESCRIPTION OF THE DRAWINGS

FIG. 2 is a table showing nuclear reactions and bombarding energies for knee irradiation;

FIG. 12 is a table of the ratios of synovium dose to skin dose, synovium dose to bone surface dose, and total time (per mA) to deliver 10,000 rad to the synovium, for different moderator lengths;

FIG. 13 is a table of results showing the effect of reflector material on therapeutic ratio and on dose rate by fixing the moderator length at 30 cm and varying the composition of the 18 cm thick reflector;

FIG. 16 is a table of the calculated therapy parameters for five neutron-producing reactions;

FIG. 22 is a table of exemplary advantage depths and RBE dose-rates (per milliampere of deuteron current) for each beam.

DETAILED DESCRIPTION OF THE ILLUSTRATED EMBODIMENTS

A. BORON NEUTRON CAPTURE SYNOVECTOMY

An exemplary embodiment of the invention involves the use of the $^{10}$B(n,α)$^7$Li nuclear reaction for the treatment of rheumatoid arthritis. Since the tissue targeted for selective treatment in rheumatoid arthritis is the synovium, the treatment is called Boron Neutron Capture Synovectomy (BNCS). There is a number of very significant differences between BNCS and Boron Neutron Capture Therapy (BNCT), a therapy technique based on the same nuclear reaction. These differences lead to different requirements for clinically-useful neutron beams.

One major difference is the depth of the target tissue. In rheumatoid arthritis, the target of therapy is the synovial membrane. This membrane lines the joint capsule and is responsible for secreting and maintaining the lubricating synovial fluid. The synovium also plays an important role in maintaining joint stability. Rheumatoid synovium is grossly inflamed and is the cause of the pain and disability associated with the disease. If treatment with anti-inflammatory agents is not successful, then methods of removing the synovium must be employed in order to limit eventual cartilage destruction.

Figure 1:
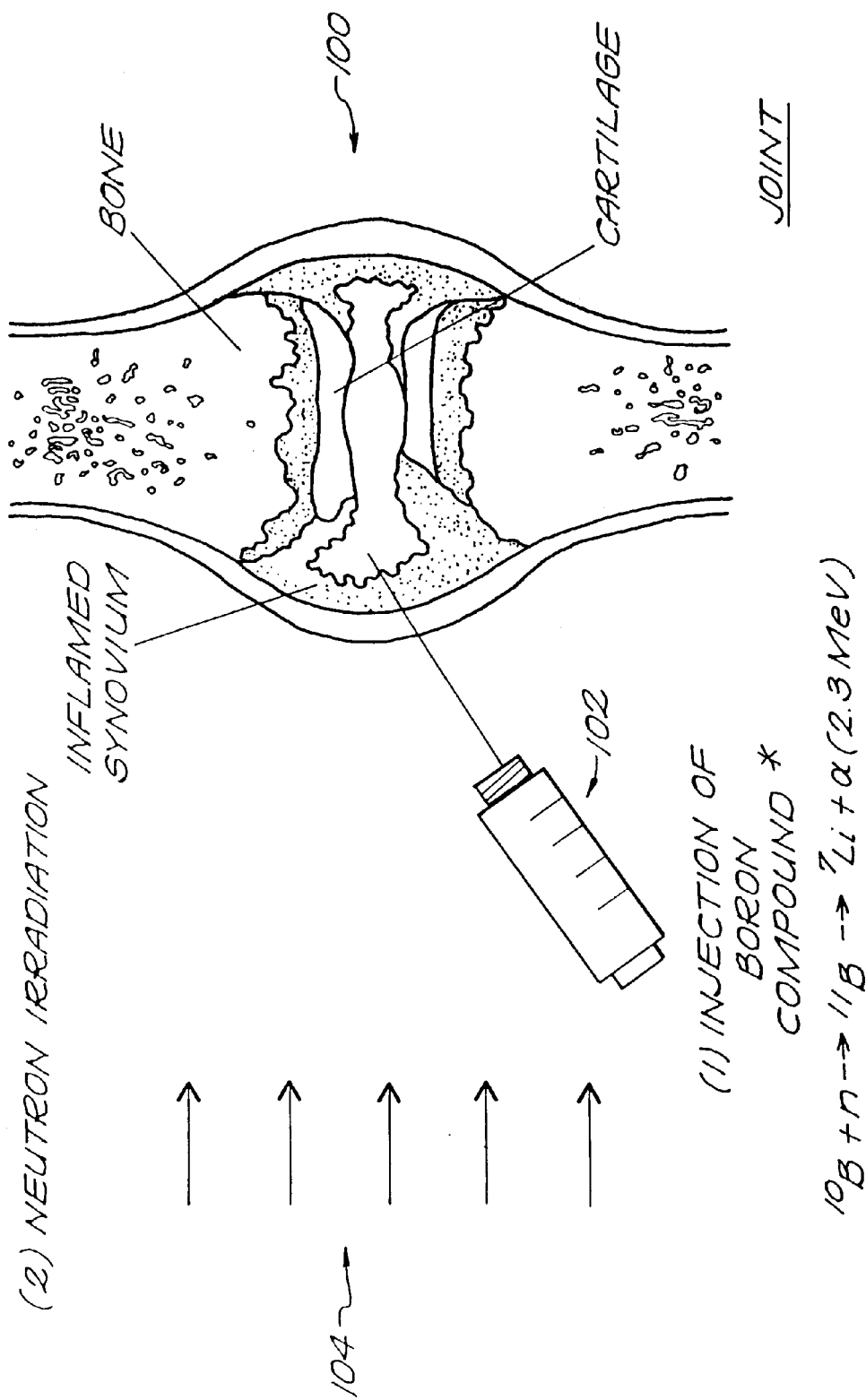
FIG. 1 is a schematic diagram of BNCS as applied to a human knee joint.

As illustrated in FIG. 1, BNCS proposes to ablate the synovium of a human knee 100 by injection of a boronated compound 102 into the synovial fluid, followed by irradiation with a beam of neutrons 104 after the compound has been taken up by the diseased synovium. It will be appreciated that elements other than boron, which have a high neutron capture or reaction cross-section, could also be used. Alternatively, exogenous elements which become radioactive due to neutron irradiation could be used. The neutron-sensitive element could be administered in any form. For, example, the elements could be in the form of a soluble or insoluble compound, a particulate, or a microsphere.

The synovial membrane lies only 1.5 to 2.0 cm below the surface of the skin. This means that a much softer neutron beam will be required than used in BNCT, where incident epithermal neutrons are needed to supply a high thermal flux to depths of as much as 7 cm. Previous investigations into the ideal neutron beam energy for BNCS have demonstrated that neutrons in the energy range from thermal up to approximately 1 keV will maximize the therapeutic ratio of the treatment and minimize the fast neutron dose at the skin surface relative to the other background dose components. This result is very different from the results of similar studies of the necessary neutron beam energy for BNCT. Extensive work has been carried out in the design of both reactor and accelerator-based neutron beams for the treatment of deep-seated (up to 7 cm) tumors. These studies have had as their goal the production of intense epithermal beams with maximum energies in the range of 10–40 keV. Thus, while some of the design considerations for epithermal beams can be of use in the invention, a number of significant differences between the clinical applications of BNCS and BNCT make those beams optimized for BNCT suboptimal for use in BNCS.

A second major difference between BNCS and BNCT is the fact that boron concentrations achievable in BNCS are likely to be very much higher than those obtained in BNCT. Incubation of human rheumatoid synovium with boron-containing compounds has led to bulk $^{10}B$ uptake levels (scaled to 100% enrichment of $^{10}B$) of 1500 to 2500 ppm and higher. It is expected that these concentrations will also be reached in vivo since the diseased synovial membrane shows extensive projections into the synovial fluid. These projections will be surrounded on almost all sides by the boronated compound which has been injected directly into the synovial fluid. Thus, a situation similar to the in vitro experiment will be created. This differs from BNCT in which the boron-labeled compound is introduced systemically and the body's physiological pathways are relied upon to transport the boronated compound to the tumor, a considerable distance away from the site of administration. The large $^{10}B$ concentrations expected in BNCS mean not only that treatment times can be very rapid for a given neutron source, but also that healthy tissue dose due to contaminant radiations (fast neutrons, gammas) will be much lower since the joint will be in the neutron beam for only a short time. It will be appreciated that higher levels of boron concentration are advantageous, the invention is also applicable to much lower concentrations of boron in the joint.

Third, the majority of articular joints are located far from the body's sensitive organs. Unlike the situation faced when irradiating brain tumors, radiation-sensitive organs are unlikely to be within the beam's field of view. Healthy tissue irradiation, therefore, is unlikely to result in acute radiation reactions. This being said, however, patients suffering from rheumatoid arthritis are otherwise healthy individuals with a long projected life span. It is very important to protect them from the potential carcinogenic effects of healthy-tissue irradiation which could be observed as many as 20 to 30 years after the treatment.

These differences between BNCS and BNCT lead to the conclusion that it is necessary to develop different beams that will be specifically useful to BNCS. In accordance with the invention, Monte Carlo calculations are used to examine a number of factors affecting beam design in BNCS and to develop a number of potential moderator/reflector configurations predicted to provide rapid therapy with large therapeutic ratio. Used as the preliminary design criterion was the maximization of neutrons in the thermal to 1 keV energy range for reasons described hereinafter. Subsequent beam optimization was carried out in a tissue-equivalent phantom of the human knee joint.

Neutron beams for BNCS could be based on any prolific neutron-producing source. Reactors are one example of high-intensity neutron sources. Charged particle accelerators are also potential neutron sources which could be used for this application. Examples of suitable accelerators include electrostatic, electrostatic quadrupole, RF quadrupole, RF linac, and cyclotron accelerators.

Figure 3:
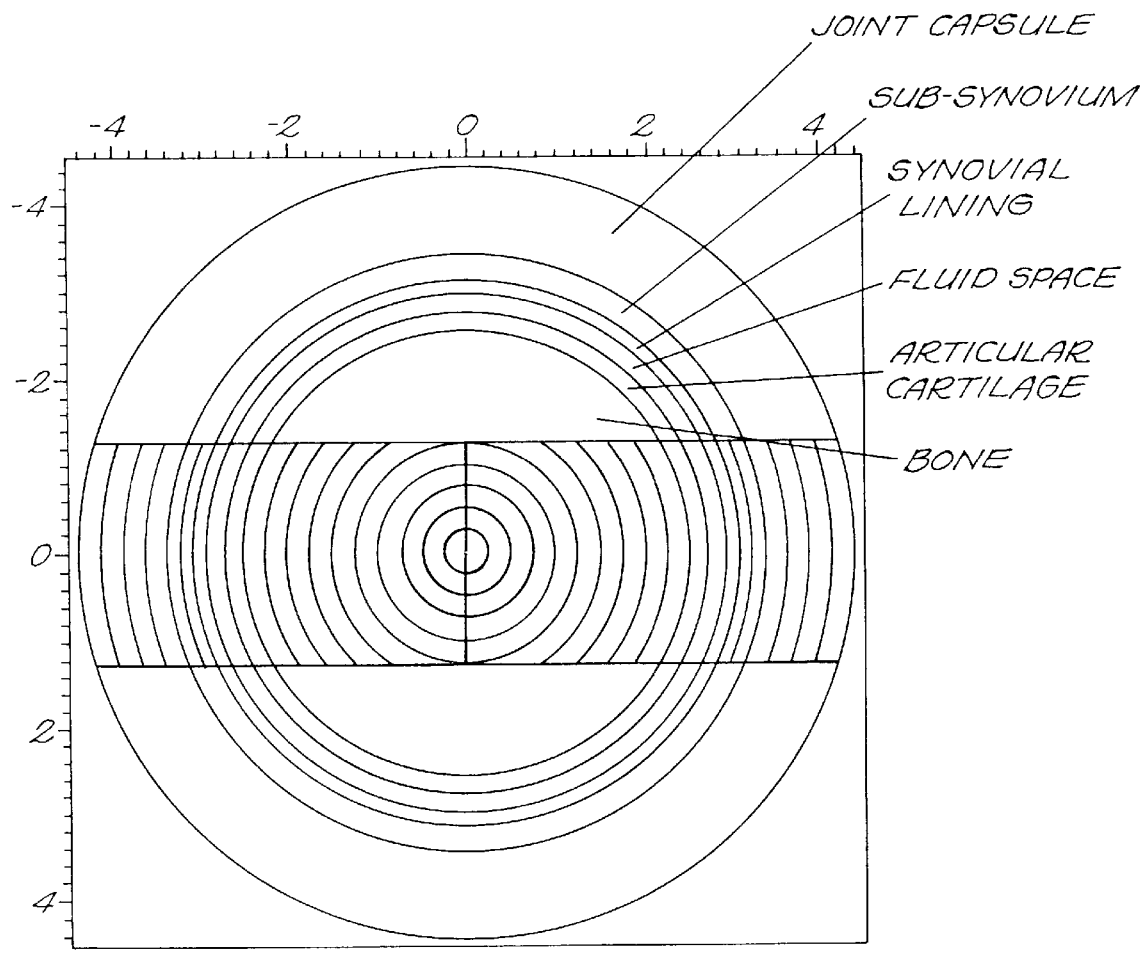
FIG. 3 is a two-dimensional illustration of a cylindrical knee joint model.

FIG. 3 is a two-dimensional illustration of a cylindrical knee joint model 300. The model consists of a series of concentric cylinders which represent the different tissue layers found in the arthritic joint. The knee was chosen as the model, since it is the joint on which surgical or radiation synovectomy is most commonly performed. The tissue thicknesses, estimated from Magnetic Resonance images of human arthritic knees are as follows: 1 cm for the joint capsule (i.e. overlying tissue), 0.3 cm for the subsynovium, 0.15 cm for the synovial lining, 0.2 cm for the joint fluid space, 0.2 cm for the articular cartilage and 5 cm for the bone. Thus, the total diameter of the joint phantom is 8.70 cm. A 10 cm diameter monoenergetic neutron beam was placed 1.65 cm away from the tissue surface. In this example, absorbed doses were tallied in a cross-section of a cylinder, with width of 2.5 cm and height of 6 cm, in the plane perpendicular to the beam.

Simulated beam energies ranged from 0.025 eV to 10 keV. Particle fluence was determined as a function of depth for all components: thermal neutrons (with a cutoff energy of 0.36 eV), fast neutrons and induced photons, including the 478 keV prompt photon emitted in the $^{10}B(n,\alpha)^7Li$ reaction. Both the neutron and photon fluxes were modified by fluence-to-kerma conversion factors.

To estimate the $^{10}B(n,\alpha)^7Li$ contribution to dose in the synovial lining, the thermal neutron flux was modified by the $^{10}B$ fluence-to-kerma conversion factors and multiplied by 400, a conservative estimate of the $^{10}B$ concentration obtained in on-going in vitro studies. A similar procedure was followed for the boron dose contribution to healthy tissue which was assumed to have 1 ppm of $^{10}B$.

The simulation code used in this investigation was the Monte Carlo for Neutron and Photon Transport (MCNP, version 4a) developed at the Los Alamos Scientific Laboratory. The advantages of MCNP over other neutron transport codes include the use of point-wise continuous cross-section data from a number of sources, three-dimensional freedom and a sophisticated geometry package to aid in design and debugging.

Figure 4A:
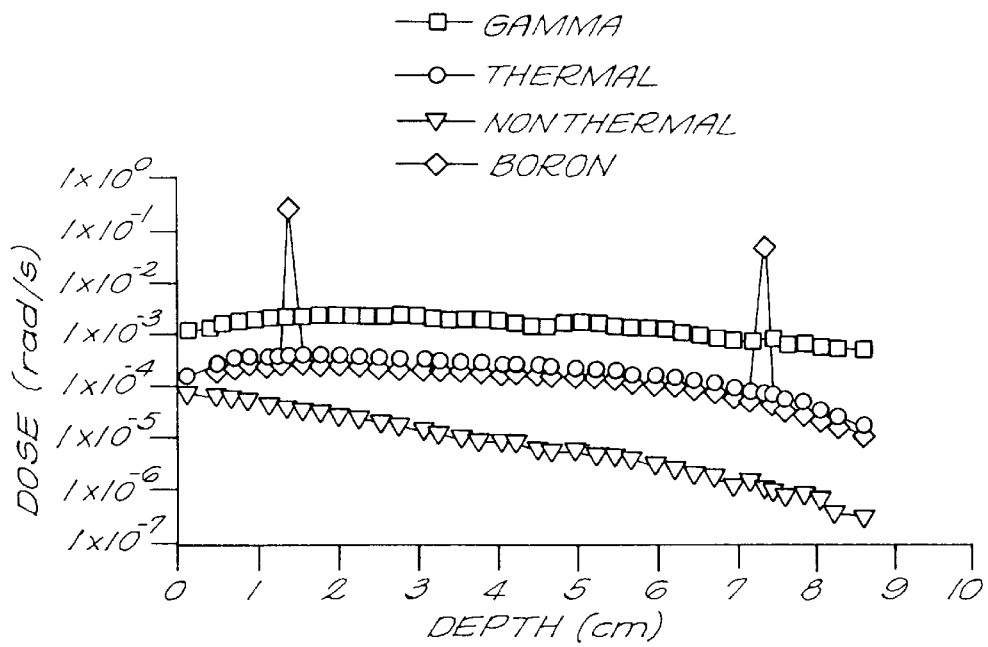
FIGS. 4A and 4B are graphs showing plots of examples of the dose components for beams of energy 10 eV and 100 keV, respectively.
Figure 4B:
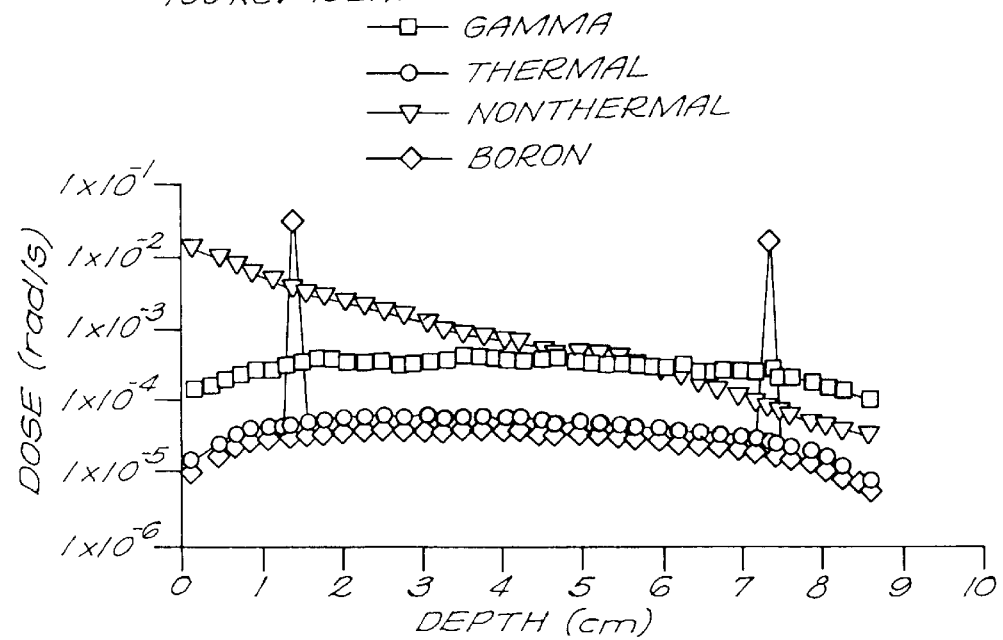

Individual dose components were plotted as a function of depth in the joint model for each energy. FIGS. 4A and 4B are graphs showing examples of the dose components for beams of energy 10 eV and 100 keV, respectively. Note that two peaks appear in the plots as a result of $^{10}B$ dose to the synovium at both the "anterior" and "posterior" of the knee model. The fast neutron dose contribution grows as neutron beam energy increases such that at 100 keV it is comparable to the boron dose contribution at the synovial lining.

Figure 5A:
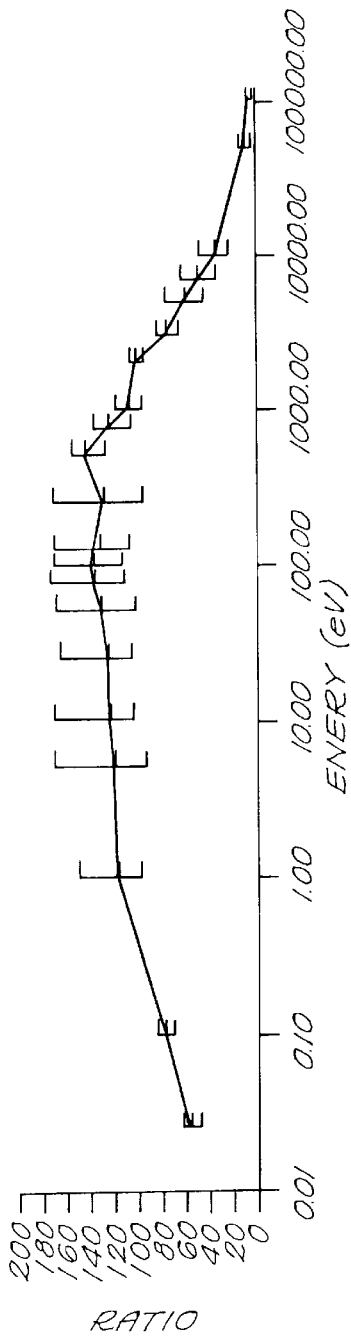
FIGS. 5A and 5B are graphs showing plots of the ratio of synovium dose to bone dose and skin dose, respectively.
Figure 5B:
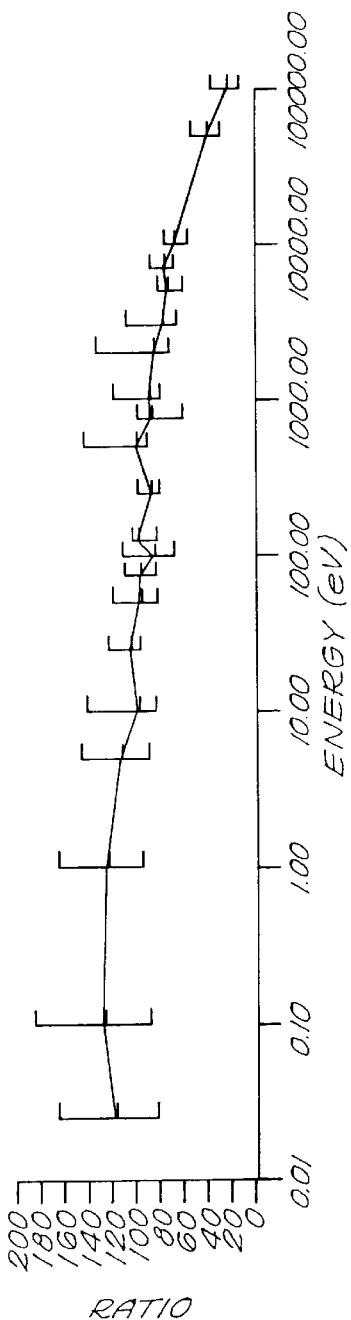

Determination of the therapeutic usefulness of the monoenergetic beams was carried out by examining the ratio of therapeutic dose to healthy tissue dose in two different regions of the phantom: the skin capsule and the bone. First, total dose was determined by summing all the dose components (no RBE weighting factors were used). The ratio of the total synovial lining dose to the healthy tissue dose was then calculated for all tissue layers and for all beam energies. Results for the ratio of synovium dose to bone or to capsule dose are shown in the graphs of FIGS. 5A and 5B. FIGS. 5A and 5B plot the ratio of synovium dose to bone dose and skin dose, respectively. Note that since dose to each tissue type was tallied over several cylinders (e.g. the bone was made up of ten separate tally regions), a number of values were obtained for each ratio. The average value is shown in FIGS. 5A and 5B with the ranges indicated by the vertical bars (i.e. these are not "error bars").

The average synovium dose to capsule dose ratio increases and reaches a plateau between about 1 eV and 500 eV. For neutron energies greater than about 500 eV, the ratio decreases monotonically. The average ratio of synovium dose to bone dose decreases slowly from thermal energies to 100 keV, the maximum energy simulated. It should be noted that both ratios have very high values (50 to 180) over this neutron range. Considering both ratios together, neutrons in the range from 0.025 eV to roughly 1 keV would maximize the therapeutic ratios for BNCS.

Ideal neutron beam studies have demonstrated that low energy neutrons, roughly in the range from thermal energies to 1 keV, will provide the highest therapeutic ratio in BNCS. This energy range, therefore, will represent a design goal in future studies aimed at modeling a useful therapy beam for a practical neutron source.

Monte Carlo calculations using MCNP were carried out to examine the ability of various moderator and reflector materials with varying dimensions to produce a neutron beam with high intensity neutrons in the thermal to 1 keV energy range with low fast neutron contamination, and to determine the neutron and photon dose-depth distributions from various neutron beams in an ideal human knee phantom. The phantom geometry and dose tally parameters are described in detail hereinafter.

The nuclear reactions investigated and the preferred ion bombarding energies for knee irradiation are listed in the table of FIG. 2. However, useful neutron beams can be produced at other ion energies. For the Li(p,n) and Be(p,n) reactions, useful neutron beams can be produced at ion energies ranging from the reaction thresholds to approximately 10 MeV. For the Be(d,n) reaction, useful ion energies range up to about 10 MeV.

Figure 6:
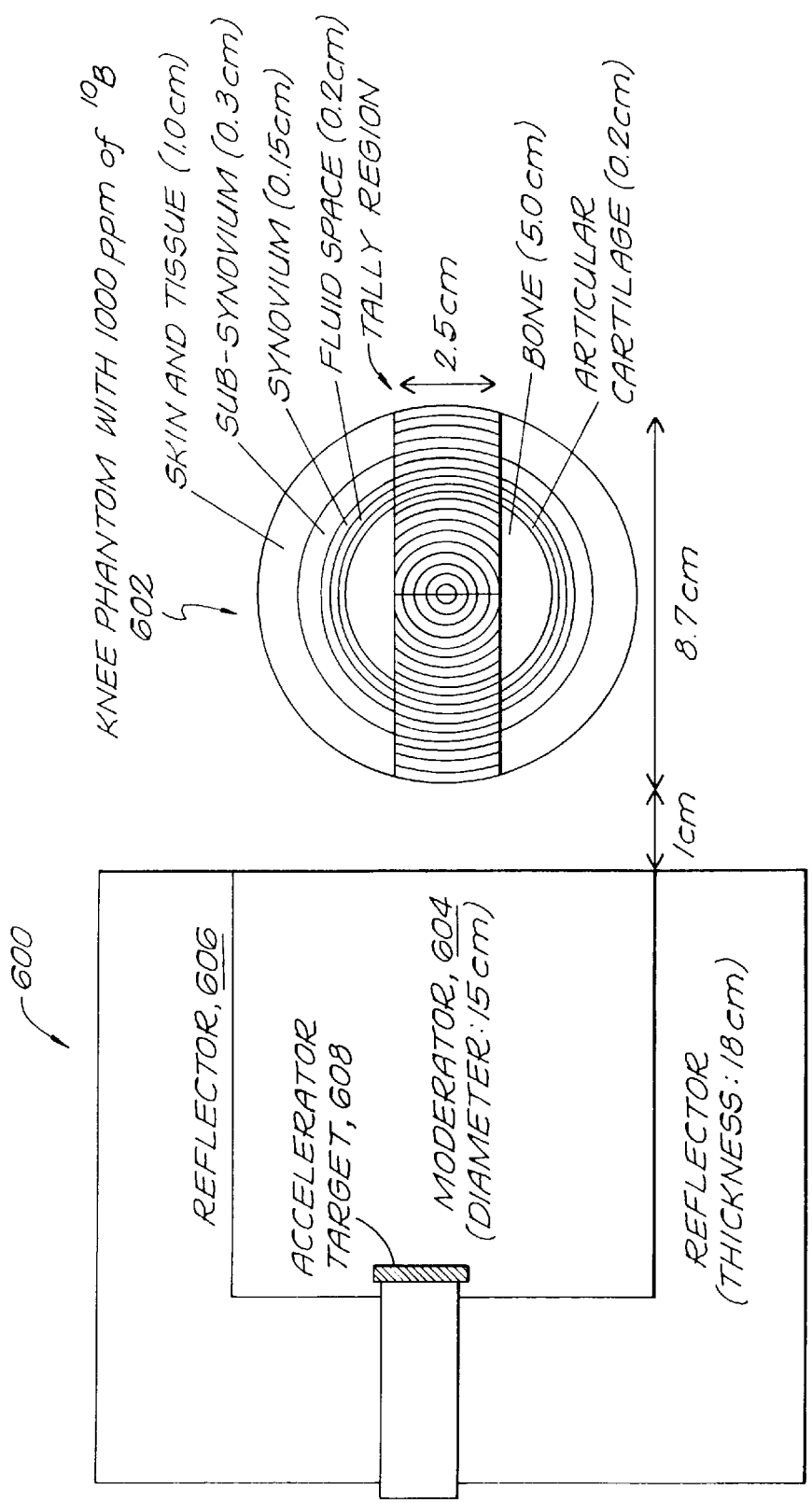
FIG. 6 is a schematic diagram of an exemplary neutron beam source and its location relative to a human knee phantom.

An exemplary neutron beam source 600, and its location relative to a human knee phantom 602 are illustrated in FIG. 6. The source 600 includes a moderator 604, a reflector 606 and an accelerator target 608.

The moderator 604 diameter shown is representative of the preferred embodiment for irradiation of the human knee. Other diameters, ranging from about 1 cm to about 25 cm are preferred for the irradiation of other joints. The reflector 606 thickness of 18 cm is preferred for the Li(p,n) reaction using 2.5 MeV protons. Other reflector thicknesses, ranging from about 5 cm to about 35 cm, are also useful, with larger thicknesses being preferred for higher neutron energies.

Parameters varied in the simulations include the target material, ion energy, and corresponding neutron energy spectrum, and the moderator and reflector materials and dimensions. The geometry shown in FIG. C1 illustrates a cylindrical moderator 604 surrounded by a simple cylindrical reflector 606 with one closed end and one open end forming the irradiation port. An opening in the closed end of the reflector 606 allows the target 608 to be inserted into the moderator volume.

Initial evaluations were carried out in air, at the patient/phantom position. Particle flux or dose was tallied across a 15 cm diameter surface 1 cm away from the end of the moderator. Later designs were evaluated in the tissue-equivalent cylindrical knee phantom consisting of soft tissue (synovium), bone, and articular cartilage tissue-equivalent materials. Tallies were obtained within a 2.5 cm diameter through a cross-section of the cylinder as shown in FIG. 6.

Thermal neutron (En<0.36 eV), non-thermal neutron and photon fluxes were converted to dose using fluence-kerma conversion factors. For most runs, a $^{10}B$ concentration of 1000 ppm was assumed to exist in the synovium, a number which could vary considerably without altering the results provided hereinafter. Because of the magnitude of this concentration, the boron in the synovium was explicitly modeled in the calculations. All healthy tissues were assumed to contain 1 ppm $^{10}B$. RBE values of 4.0 for the $^{10}B$ reaction products, 3.8 for all neutrons, and 1.0 for photons, were used. It will be appreciated that other RBE values could have been used.

The potential clinical efficacy of the neutron beam produced by each configuration of materials was determined by examining the ratio of target (synovium) dose to each of two different healthy tissues. The first healthy tissue was the skin surface. Radiation effects in the skin are non-stochastic indicating that a threshold dose must be reached before the effect is observed.

A mild skin reddening, which is not permanent, is seen at doses of approximately 800 rad. If a therapeutic dose of 10,000 rad is delivered to the boron-loaded synovium (an empirical estimate of the dose required to produce a clinical effect in radiation synovectomy, a procedure in which beta-emitters are injected into the joint to cause synovial ablation), then the ratio of synovium dose to skin dose is preferably greater than 12 if skin erythema is to be avoided. It will be appreciated that the erythema appearing at a dose of approximately 800 rad is a minor and temporary condition. Therefore, therapeutic ratios less than 12 (e.g. 4) will be both clinically useful and well tolerated.

The second healthy tissue of interest is the bone surface. The International Commission on Radiological Protection has identified the bone surface as a tissue to be protected whenever possible during radiotherapy procedures involving the bone. Potential effects (cancer induction) are stochastic indicating that there is no threshold and the probability of effect increases with dose. Thus, no dose limits as such are set. A goal in this study was therefore to maximize the target (synovium) to bone surface dose ratio in order to limit the potential carcinogenic effects.

For all of the reactions listed in the table of FIG. 2, the maximum neutron energy is relatively high. Thus, to reach the design goal of a 0.025 eV–1 keV beam, moderation of the source neutrons must take place. Note that, unlike the situation encountered in the design of epithermal beams for the treatment of deep seated cancer, over-moderation of the neutrons is not a concern and a very low Z material will be optimum here. However, like neutron beams for BNCT, fast neutron contamination and photons created via (n,γ) reactions in the moderating and reflecting materials must be minimized.

Thus, materials with large amounts of $^2$H rather than $^1$H will provide rapid energy loss without the generation of an intense photon flux. $D_2O$ was chosen as a convenient moderating material. Graphite was also investigated as a moderating material. The goal of this study was to design a clinically-useful beam for the treatment of knee joints and therefore the moderator diameter was set at 15 cm. It is likely that different diameter beams would optimize the treatment of other articular joints (wrists, fingers, etc.) and alternative beams will be evaluated in the future.

A neutron reflector is placed around the moderator to improve the yield of therapy neutrons at the irradiation position. Any neutron leaving the moderator in a direction not compatible with patient treatment may scatter in the reflector, scattering back into the moderator, now having a second chance of becoming a "therapy" neutron. Again, a material with low gamma production is needed. In accordance with the invention, it is likely that moderation of the neutrons in the reflector will be desirable since the ultimate goal is a beam of relatively low energy neutrons. This is unlike the situation when designing epithermal beams for the treatment of deep seated cancer, in which case the goal is as little energy loss within the reflector as possible.

Several reflector materials were examined including graphite, lead, $^7Li_2CO_3$, and $D_2O$ (i.e. simply extending the diameter of the moderator). As a result of previous work demonstrating that the number of neutrons in all energy bins asymptotically reaches a maximum at roughly 18 cm, the radial reflector thickness was set at this value (or 15 cm in the earliest calculations). The exemplary reflector extended 5 cm in the backwards direction as shown in FIG. 6, however, other thicknesses could be used.

Figure 7A:
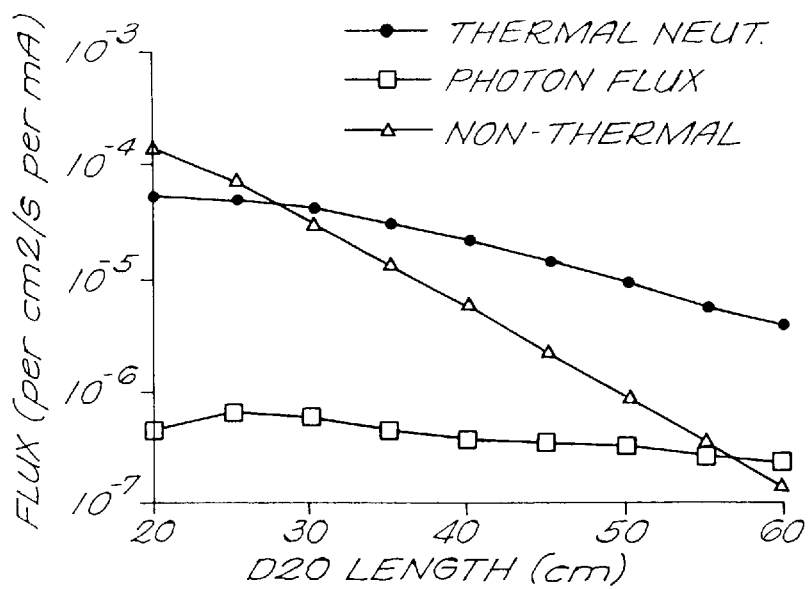
FIGS. 7A and 7B are graphs showing plots of particle flux as a function of $D_2O$ length for the $^7$Li(p,n) neutron source and the $^9$Be(p,n) neutron source, respectively.
Figure 7B:
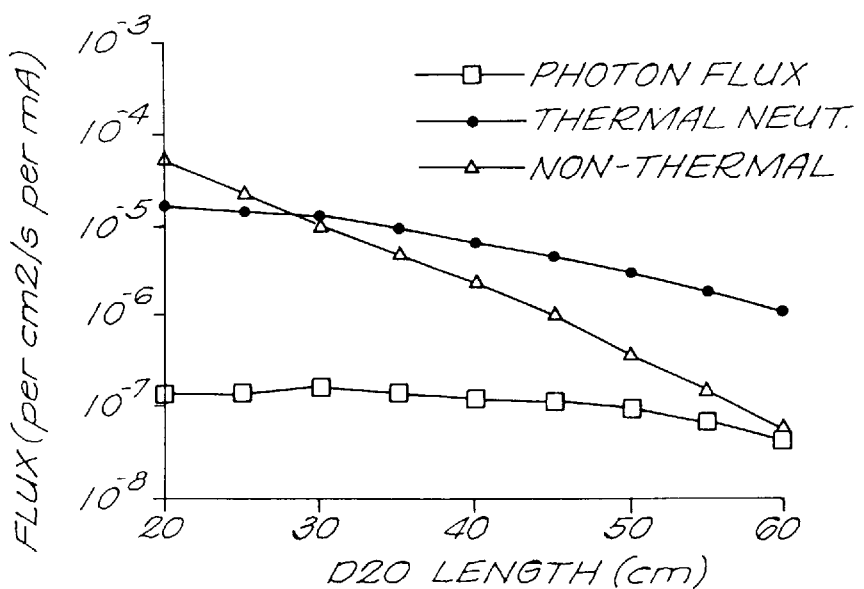

An example of the ability of $D_2O$ to moderate the source neutrons from the $^7Li(p,n)$ ($E_p$=2.5 MeV) and the $^9Be(p,n)$ ($E_p$=4.0 MeV) reactions is illustrated in the graphs of FIG. 7A and 7B, which plot the thermal neutron (<0.36 eV), non-thermal neutron, and photon fluxes as a function of $D_2O$ length. FIGS. 7A and 7B show a plot of particle flux as a function of $D_2O$ length for the $^7Li(p,n)$ neutron source and the $^9Be(p,n)$ neutron source, respectively.

Figure 8A:
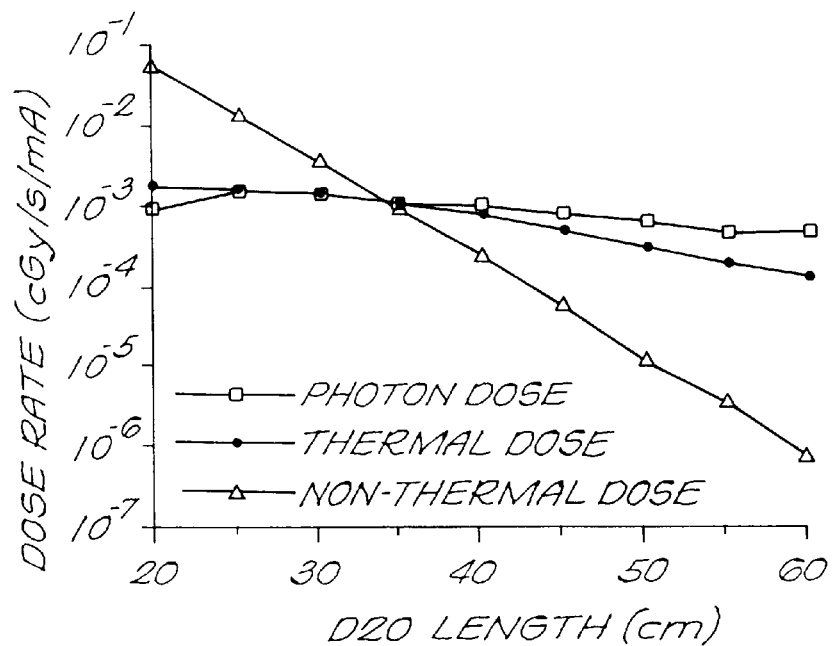
FIGS. 8A and 8B are graphs showing plots of dose rate per milliampere of proton current for photons, thermal neutrons and nonthermal neutrons as a function of $D_2O$ length for the $^7$Li(p,n) neutron source and the $^9$Be(p,n) neutron source, respectively.
Figure 8B:
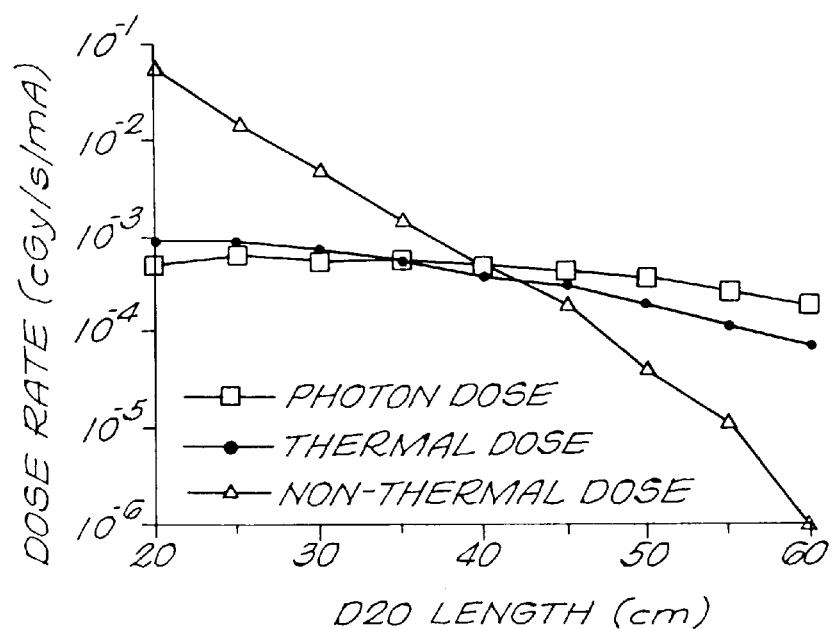

FIGS. 8A and 8B are graphs showing the corresponding dose rates per mA of proton current. Accordingly, FIGS. 8A and 8B plot dose rate per milliampere of proton current for photons, thermal neutrons and nonthermal neutrons as a function of $D_2O$ length for the $^7Li(p,n)$ neutron source and the $^9Be(p,n)$ neutron source, respectively. The moderator in this example is 15 cm in diameter and is surrounded by a cylindrical graphite reflector of thickness 15 cm.

The lower yield of the Be(p,n) reaction, relative to Li(p,n), is reflected in the lower flux and lower dose-rate per mA of current. The harder neutron spectrum emerging from the beryllium target is also reflected in the need for more moderating material than the lithium reaction before the non-thermal flux and dose profiles become no longer the dominant contributor to the total.

As seen in FIG. 7A, the fast neutron flux for the Li reaction is dominant until 27 cm of $D_2O$, and until 30 cm for the Be reaction. The effect becomes more evident when dose is examined.

As seen in FIGS. 8A and 8B, non-thermal dose remains the dominant component until 40 cm of $D_2O$ in the case of beryllium, and until only 35 cm in the case of the lithium target. At these moderator lengths there is a cross-over point at which the photon and thermal neutron doses become dominant. Since these components are unavoidable (the first as a result of the need for thermal neutrons to induce the B(n,α) reaction, and the second due to the n,γ reactions in both $^1$H and the $^{10}$B itself), there may be no need to reduce the fast neutron component even more by further moderation since this would also have the effect of reducing dose rate. To evaluate these assumptions, the effect of three different moderator lengths on each source spectrum was examined in a tissue-equivalent phantom.

FIGS. 9A-9B, 10A-10B and 11A-11B are graphs showing the various dose components versus depth in the knee phantom as a result of neutron beams moderated by 20, 35 and 50 cm of $D_2O$, respectively. Data for both the lithium and the beryllium sources are shown. Again it is seen that the much harder $^9Be(p,n)$ spectrum leads to a much higher non-thermal neutron dose than is seen with the $^7Li(p,n)$ reaction. Note that a harder beam could be clinically acceptable provided there is sufficient boron in the diseased tissue.

Figure 9A:
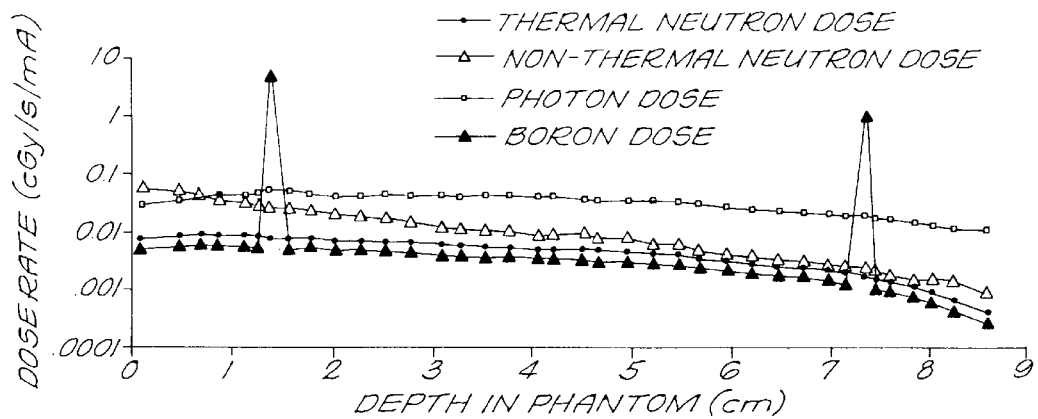
FIGS. 9A and 9B are graphs showing plots of individual dose-rate profiles through the tissue-equivalent phantom using the $^7$Li(p,n) neutron source or the $^9$Be(p,n) neutron source with a moderator length of 20 cm, respectively.
Figure 9B:
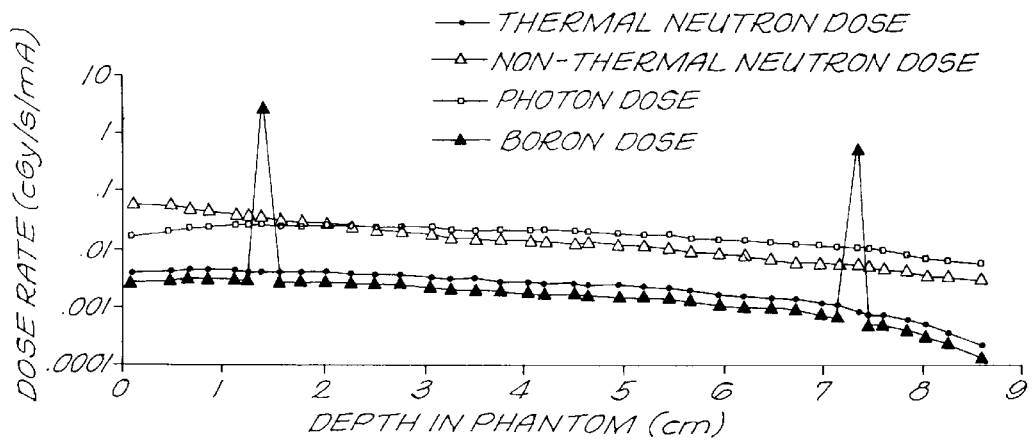

FIGS. 9A and 9B plot individual dose-rate profiles through the tissue-equivalent phantom using the $^7Li(p,n)$ neutron source or the $^9Be(p,n)$ neutron source, respectively. The moderator length is 20 cm. The phantom consists of skin and soft tissue (0–1.3 cm), synovium (1.3–1.45 cm), synovial fluid (1.45–1.65 cm), articular cartilage (1.65–1.85 cm) and bone (1.85–6.85 cm). Since the model is cylindrical, the tissue components are repeated. Hence, the two boron dose peaks are a result of $^{10}$B in the synovium at the front and back of the model.

Figure 10A:
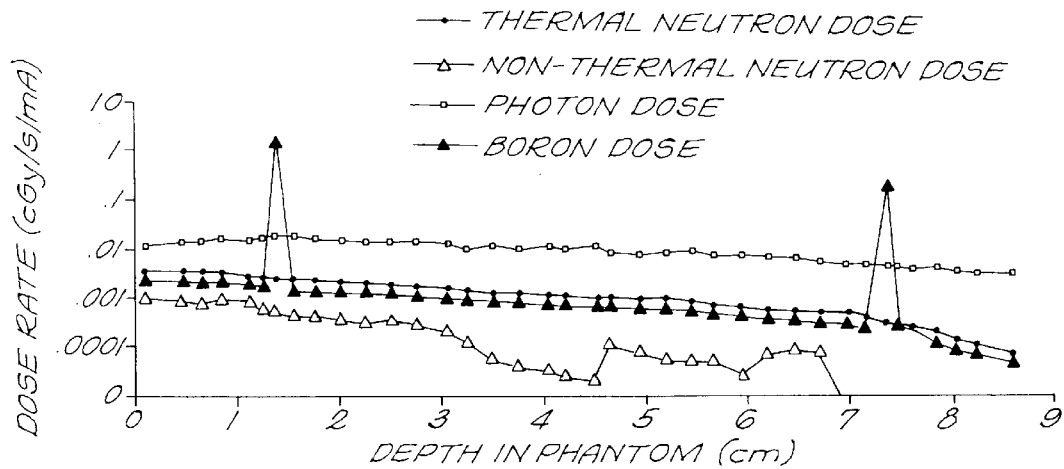
FIGS. 10A and 10B are graphs showing plots of individual dose-rate profiles through the tissue-equivalent phantom using the $^7$Li(p,n) neutron source or the $^9$Be(p,n) neutron source with a moderator length of 35 cm, respectively.
Figure 10B:
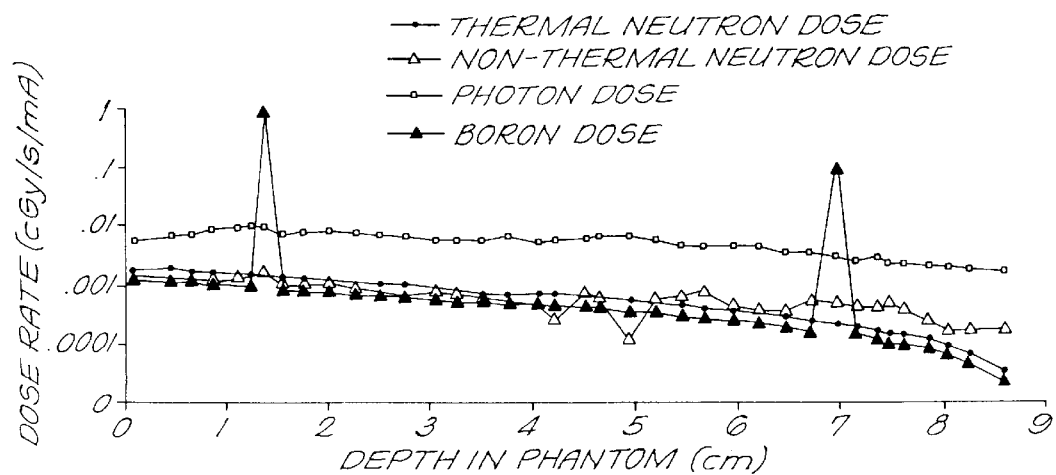

FIGS. 10A and 10B plot individual dose-rate profiles through the tissue-equivalent phantom using the $^7Li(p,n)$ neutron source or the $^9Be(p,n)$ neutron source, respectively. The moderator length is 35 cm.

Figure 11A:
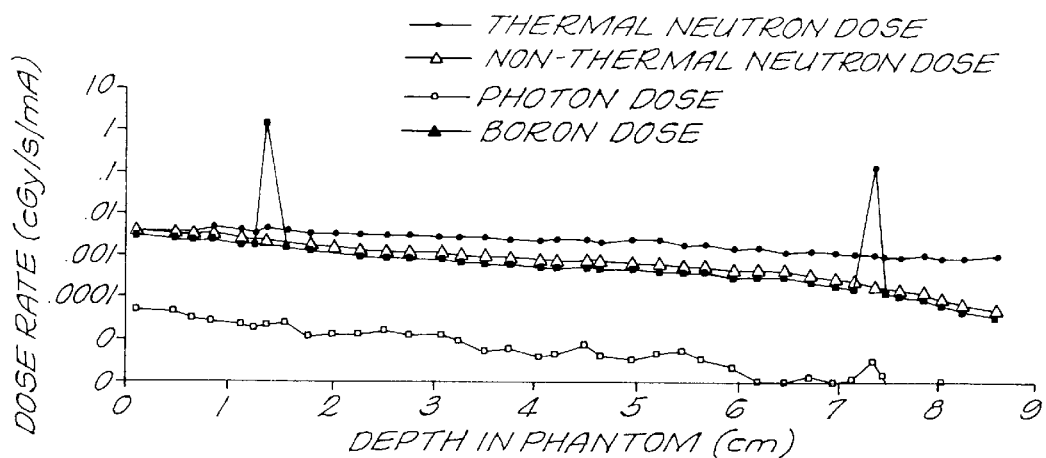
FIGS. 11A and 11B are graphs showing plots of individual dose-rate profiles through the tissue-equivalent phantom using the $^7$Li(p,n) neutron source or the $^9$Be(p,n) neutron source with a moderator length of 50 cm, respectively.
Figure 11B:
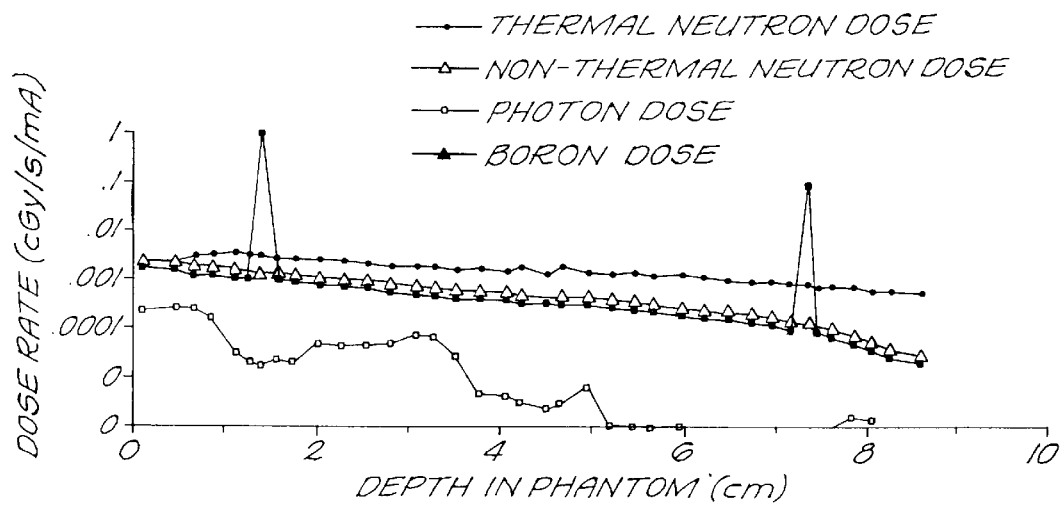

FIGS. 11A and 11B plot individual dose-rate profiles through the tissue-equivalent phantom using the $^7Li(p,n)$ neutron source or the $^9Be(p,n)$ neutron source, respectively. The moderator length is 50 cm.

The consequences of different moderator lengths are quantified in the table of FIG. 12 which shows for this example the ratios of synovium dose to skin dose, synovium dose to bone surface dose, and total time (per mA) to deliver 10,000 rad to the synovium, for each case. In all cases the therapeutic ratio for the skin greatly exceeds the conservative design goal of 12. Total time to deliver 10,000 cGy to the target tissue ranges from 7 minutes to just over one hour, per milliampere of proton current.

The effect of reflector material on therapeutic ratio and on dose rate for this example was investigated by fixing the moderator length at 30 cm and varying the composition of the 18 cm thick reflector. Example results using $D_2O$ as the moderating material are shown in the table of FIG. 13 which tabulates therapeutic ratios and total therapy time, per mA. Also shown in FIG. 13 is the effect of using graphite as the moderating material, showing that a graphite moderator can also be used to produce a favorable therapy beam. In all cases the source neutrons are from the $^9Be(p,n)$ reaction.

The effect of the neutron reflector is clear in two respects. First, the absence of any reflector leads to a dose rate that is 200–300 times lower in the phantom. This is a much larger effect than is seen when designing beams for BNCT in which a moderator with a much larger diameter is used. Similarly, beams designed for the treatment of smaller joints are likely to depend even more heavily on the ability of the reflector to maintain the neutrons within the assembly volume.

Second, the importance of the ability of the reflector material to moderate neutrons as well as reflect them is very evident. Thus, the poorest reflector material for this application is lead, leading both to the lowest dose rates and to the lowest therapeutic ratios. A $D_2O$ reflector provides the softest beam and hence the best therapeutic ratios, however the dose rate is not as high as with the graphite reflector. This is likely due to $D_2O$'s relatively poor ability to reflect the neutrons, thereby allowing greater leakage from the sides of the assembly. The highest dose rate is provided by a graphite reflector which is also sufficiently low-Z to substantially soften the beam leading to very advantageous therapeutic ratios.

Figure 14A:
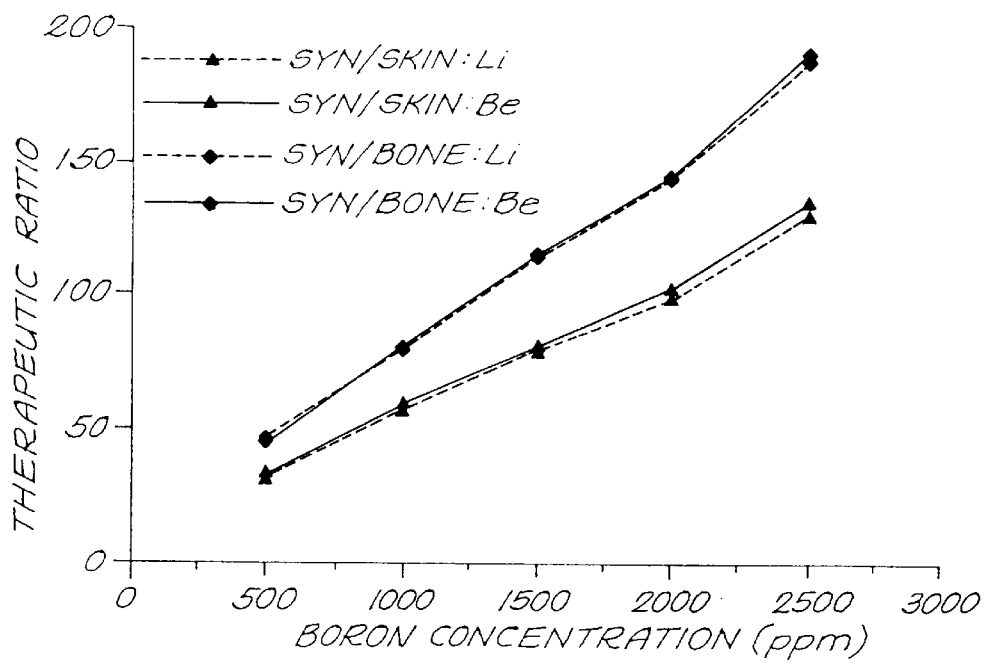
FIGS. 14A and 14B are graphs showing plots of therapeutic ratios as a function of $^{10}$B concentration in the synovium for $^9$Be(p,n) neutron beams moderated by 20 cm or 30 cm $D_2O$, and therapy time required to deliver 100 Gy to the synovium as a function of $^{10}$B concentration for the two moderated beams plotted in FIG. 14A, respectively.
Figure 14B:
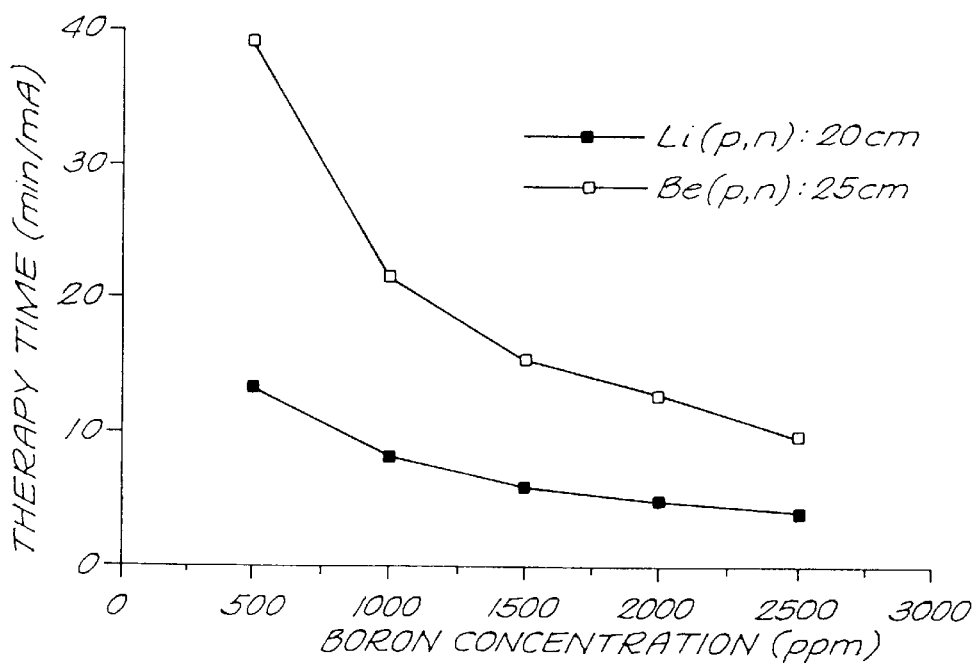

The concentration of $^{10}B$ in the diseased synovial membrane will affect the total time required to deliver the desired dose. Total therapy time will, in turn, affect the therapeutic ratios since the longer the joint is in the beam, the greater the healthy tissue dose delivered. FIGS. 14A and 14B are graphs plotting therapeutic ratios as a function of $^{10}B$ concentration in the synovium for $^9Be(p,n)$ neutron beams moderated by 20 cm or 30 cm $D_2O$, and therapy time required to deliver 100 Gy to the synovium as a function of $^{10}B$ concentration for the two moderated beams plotted in FIG. 14A, respectively. Note that the range of boron levels shown in FIGS. 14A and 14B is many times larger than the uptake levels typically observed in BNCT. However, these levels have been easily achieved in in vitro studies of boron uptake in arthritic synovium and are expected to be obtained in vivo, so long as the boronated compound is retained in the joint space and in the synovium for sufficiently long periods of time. It is clear from FIG. 14B that higher $^{10}B$ concentrations result in even more favorable therapy parameters, and that lower $^{10}B$ concentrations may also be useful, with the lower limit depending on the neutron source strength and energy spectrum and the practical limits on irradiation time. Boron uptake and retention in vivo is the subject of ongoing investigation of BNCS.

In order to approach the design goal of neutrons in the thermal to 1 kev energy range, more and more moderating material is necessary. As the moderator length is increased, however, dose rate at the patient position is reduced as more and more neutrons are captured or leak out of the assembly. As seen in FIGS. 9A and 9B it is still possible to obtain high therapeutic ratios using a somewhat energetic neutron beam. While the goal is to design a beam with a therapeutic ratio of at least 12 in order to limit the radiation dose to the skin during treatment, this goal may be within reach of an even higher-energy beam by taking advantage of multi-directional irradiation. That is, by irradiating the arthritic joints from a number of different directions (taking care not to allow the beams to overlap at the joint surface), a lower therapeutic ratio than 12 could be acceptable. Because it will be important not to allow the different beams to irradiate the same area of skin more than once, precise positioning of the joint relative to the beam direction will be necessary. The best way to do this is to immobilize the joint and to permit the neutron beam to move around the joint.

Figure 15:
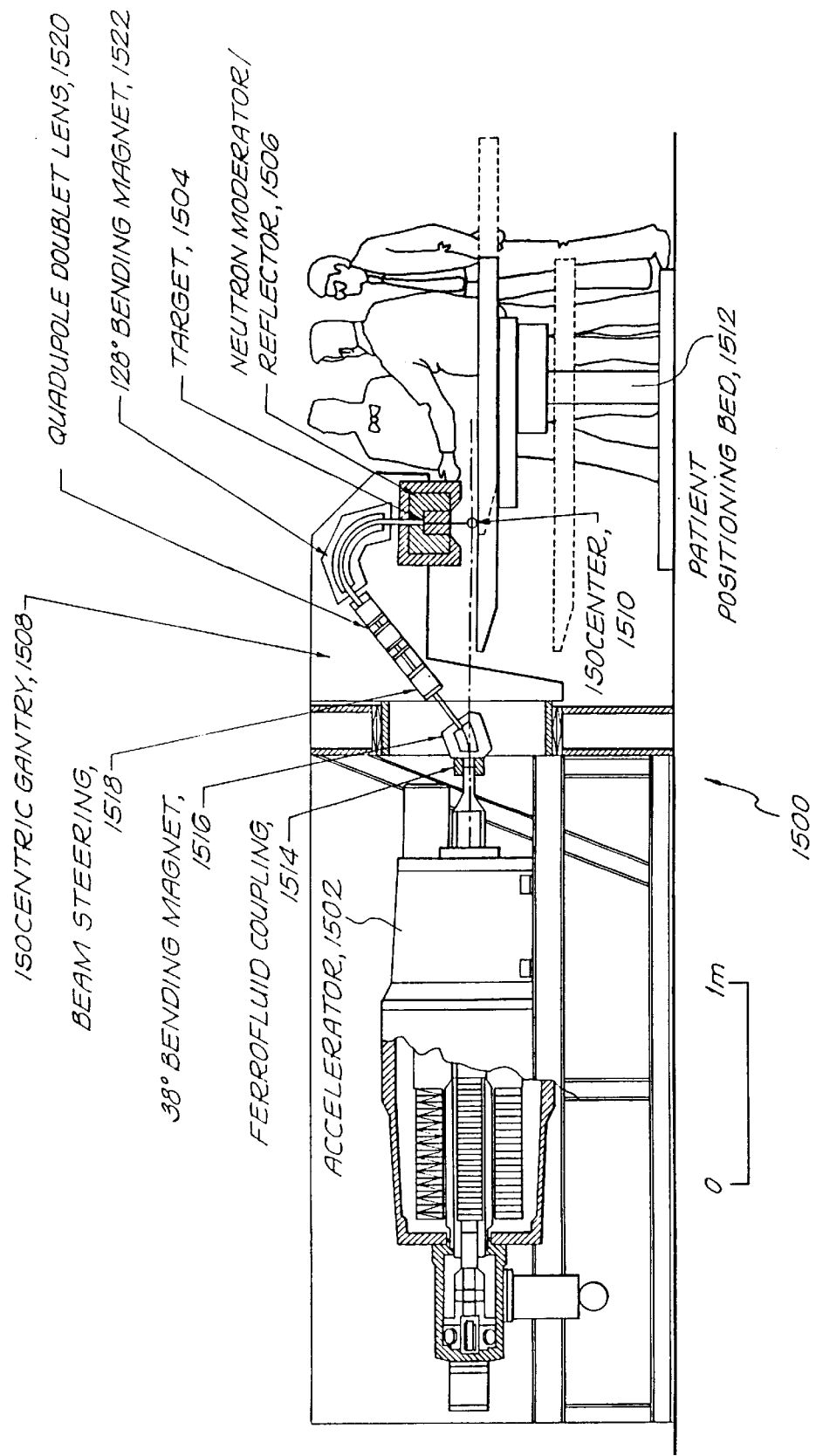
FIG. 15 is a schematic diagram of an exemplary embodiment of an isocentric gantry system.

This multi-directionality can be achieved by using an isocentric gantry system such as the exemplary system 1500 illustrated in FIG. 15. FIG. 15 is a schematic diagram of an exemplary embodiment of an isocentric gantry system using as a neutron source a 4.1 MeV tandem electrostatic accelerator 1502. The accelerator is based on a compact tandem electrostatic accelerator designed by Newton Scientific Inc. of Cambridge, Mass. It is under 4 m in length and weighs approximately 1000 kg. An accelerator target 1504 and neutron moderator/reflector 1506 are shown mounted on an isocentric gantry 1508 to define an isocenter 1510. The gantry 1508, in combination with a patient positioning system 1512, will allow complete three-dimensional freedom in the beam delivery direction. The beam is directed to the target using a rotatable beamline with deflection magnets, including a ferrofluid coupling 1514, a bending magnet 1516, a beam steering assembly 1518, a quadupole doublet lens 1520, and a bending magnet 1522.

The system 1500 will allow complete freedom in the azimuthal position of the neutron beam moderator and reflector assembly with respect to the horizontal axis. The gantry comprises a rotatable support structure to which the moderator assembly, neutron-producing target, vacuum beamline and ion beam optics are mounted. After exiting the accelerator, the proton beam is transported to the target using the bending magnets. X-Y steering plates and a magnetic quadruple doublet lens mounted between the bending magnets allow control of the beam position and diameter at the target location. The gantry vacuum beamline is connected to the accelerator beamline by the ferrofluid coupling, allowing the gantry to be rotated without breaking vacuum anywhere in the system. The gantry mechanical support structure will be designed to carry weights of up to at least 5 tons and to achieve a spatial positional tolerance of 5 mm at the isocenter. This is well within the parameters of existing neutron therapy gantries and will accommodate any of the moderator/reflector designs described above. Further calculational studies will be carried out to quantitatively evaluate the improvement in treatment time possible with multi-directional irradiations.

This study of neutron beam design for Boron Neutron Capture Synovectomy has demonstrated that low-energy neutron beams can be generated resulting in both high dose rate and very large therapeutic ratios. These beams can be based on either neutrons generated by nuclear reactors or charged particle reactions with the preferable beams produced using a $D_2O$ moderator and a graphite reflector. A tandem electrostatic accelerator capable of generating the proton beam currents required to create the dose rates described here is operational at MIT's Laboratory for Accelerator Beam Applications (LABA). Experimental studies to verify that the $^{10}B$ concentrations obtained in vitro can be reproduced in vivo are underway using a rabbit model of arthritis. Future work in beam design for BNCS will involve the investigation of small-diameter beams for treatment of small articular joints, and for use with an isocentric gantry system which will be used for multi-dimensional joint irradiations.

Examples of beams based on charged particle reactions include the $^9Be(d,n)^{10}B$, $^9Be(p,n)^9B$, $^7Li(p,n)^7Be$, $t(d,n)^4He$, and $d(d,n)^3He$ nuclear reactions, which have been evaluated as neutron sources for boron neutron capture synovectomy (BNCS). Therapeutically useful neutron beams can be produced using each of these reactions with appropriate neutron moderator and reflector configurations.

The $^9Be(d,n)^9B$ has several advantages for BNCS applications. This reaction is the most prolific of the commonly-used light ion neutron-producing reactions for ion energies in the range of approximately 1–3 MeV, and has the further advantage that beryllium has excellent thermal and mechanical properties as an accelerator target material.

With the proper choice of neutron moderator and collimator materials and geometry, the $^9Be(d,n)$ reaction provides a very attractive neutron source for BNCS when compared with the less practical $^7Li(p,n)$ source at comparable bombarding ion energy (approximately 2.5 MeV). Furthermore, a therapeutic neutron beam can also be generated using this reaction at the deuteron beam energies and currents typical of existing hospital-based biomedical cyclotrons (6–10 MeV).

Monte-Carlo simulations have been performed using the MCNP code to determine the neutron and photon dose-depth distributions from various neutron beams in an ideal knee phantom as described with reference to FIG. 6. The moderator diameter shown is representative of the preferred embodiment for irradiation of the human knee. Other diameters, ranging from about 1 cm to about 25 cm are preferred for the irradiation of other joints. The reflector thickness of 18 cm is preferred for the Li(p,n) reaction using 2.5 MeV protons. Other reflector thicknesses, ranging from about 5 cm to about 35 cm, are also useful, with larger thicknesses being preferred for higher neutron energies.

Parameters varied in the simulations include the target material, ion energy, and corresponding neutron energy spectrum, and the moderator and reflector materials and dimensions. In the simulations described hereinafter, moderator lengths ranging from 20 cm to 50 cm were used. Other moderator lengths, ranging upward from about 1 cm, are also useful depending on the target neutron energy spectrum, with larger lengths being preferred for more energetic neutrons. Other variations on this geometry are also possible, including the use of more than one reflector or moderator material, the use of different reflector thicknesses in different regions, and the inclusion of layers of neutron filter materials.

The calculated therapy parameters for five neutron-producing reactions are shown in the table of FIG. 16. In each case, a $D_2O$ moderator and graphite reflector were used. Therapeutically useful neutron beams can be produced using the (p,n) or (d,n) reactions listed in the table of FIG. 16 with various moderator lengths.

B. DEUTERON BASED REACTIONS FOR BNCT

Another exemplary embodiment of the invention provides for the use of deuteron-based charged particle reactions, such as d-Be, as sources for epithermal or thermal neutron beams for neutron capture therapies (for the treatment of cancer, arthritis and other diseases). Many d,n reactions (e.g. using deuteron, tritium or beryllium targets) are very prolific at relatively low deuteron energies. The advantage of high neutron yield however, is offset by the fact that these reactions have positive Q-values leading to the emission of high energy neutrons at even low particle bombarding energies.

As an example, using the Monte Carlo code MCNP (Monte Carlo for Neutron and Photon Transport), several (d,n) reactions were investigated in detail to determine their potential for generating clinically useful epithermal and thermal beams with sufficient intensity and low fast neutron contamination. These include d-Be (up to 7 MeV deuterons on beryllium, but preferably less than 2.0 MeV), d-d and d-t reactions. Moderator materials examined included $D_2O$, $Al/AlF_3$ and $Al_2O_3$; lead, graphite and $Li_2CO_3$ were investigated as potential reflector materials. Beam assessment was carried out both in air and in tissue equivalent phantoms of the brain and knee joint.

In this example, the dosimetry of neutrons produced by 2.6 MeV deuterons on a beryllium target is evaluated in tissue-equivalent phantoms. Investigation is carried out by computer simulation using MCNP, and experimental measurement using a high-current, 4.1 MeV tandem accelerator in conjunction with a moderator/reflector assembly and an elliptical brain phantom. Other suitable charged particle accelerators which could produce the 2.6 MeV beam include electrostatic, electrostatic quadrupole, RF quadrupole, RF linac, and cyclotron accelerators.

Figure 17:
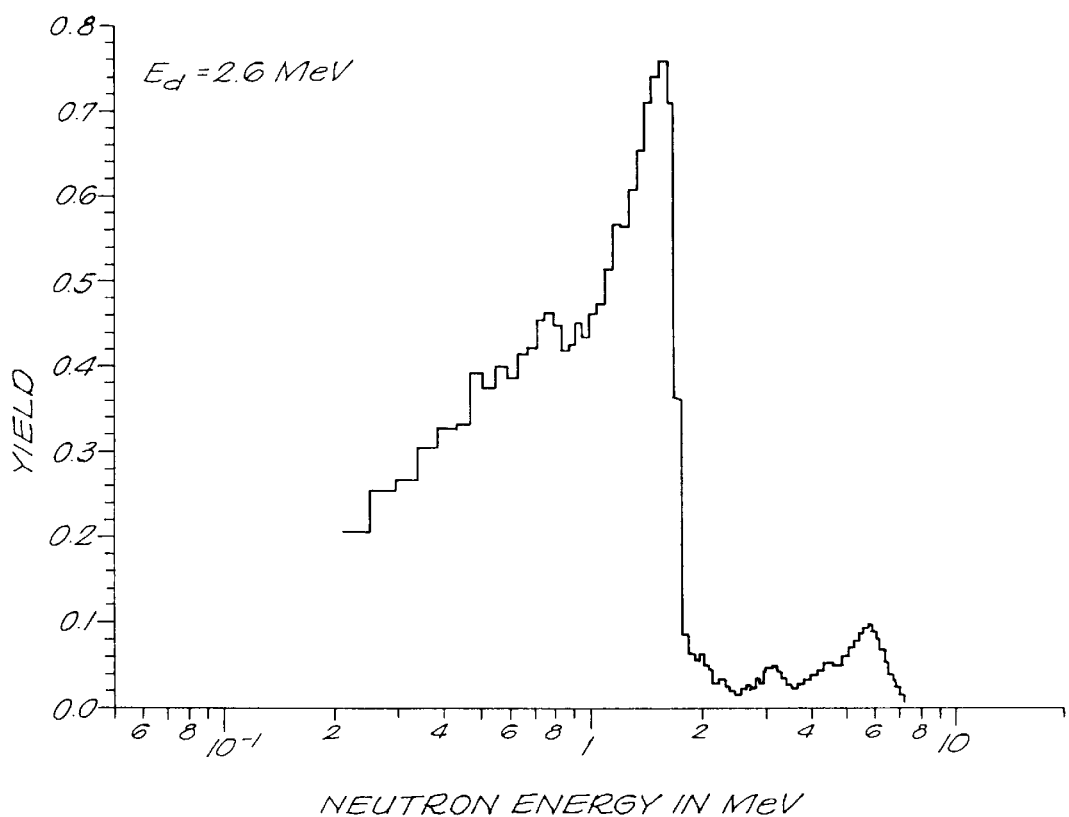
FIG. 17 is a graph of the neutron energy spectrum resulting from 2.6 MeV deuteron bombardment of a thick beryllium target.

The neutron energy spectrum resulting from 2.6 MeV deuteron bombardment of a thick beryllium target is shown in the graph of FIG. 17.

The dosimetry of Be(d,n) neutron beams in combination with different moderator/reflector assemblies was evaluated in a cylindrical brain-equivalent phantom. Various deuteron energies leading to a number of different neutron spectra were examined. Neutron emission was assumed to be isotropic. Dosimetric evaluation was carried out with the MCNP simulation code using methods previously described.

Figure 18:
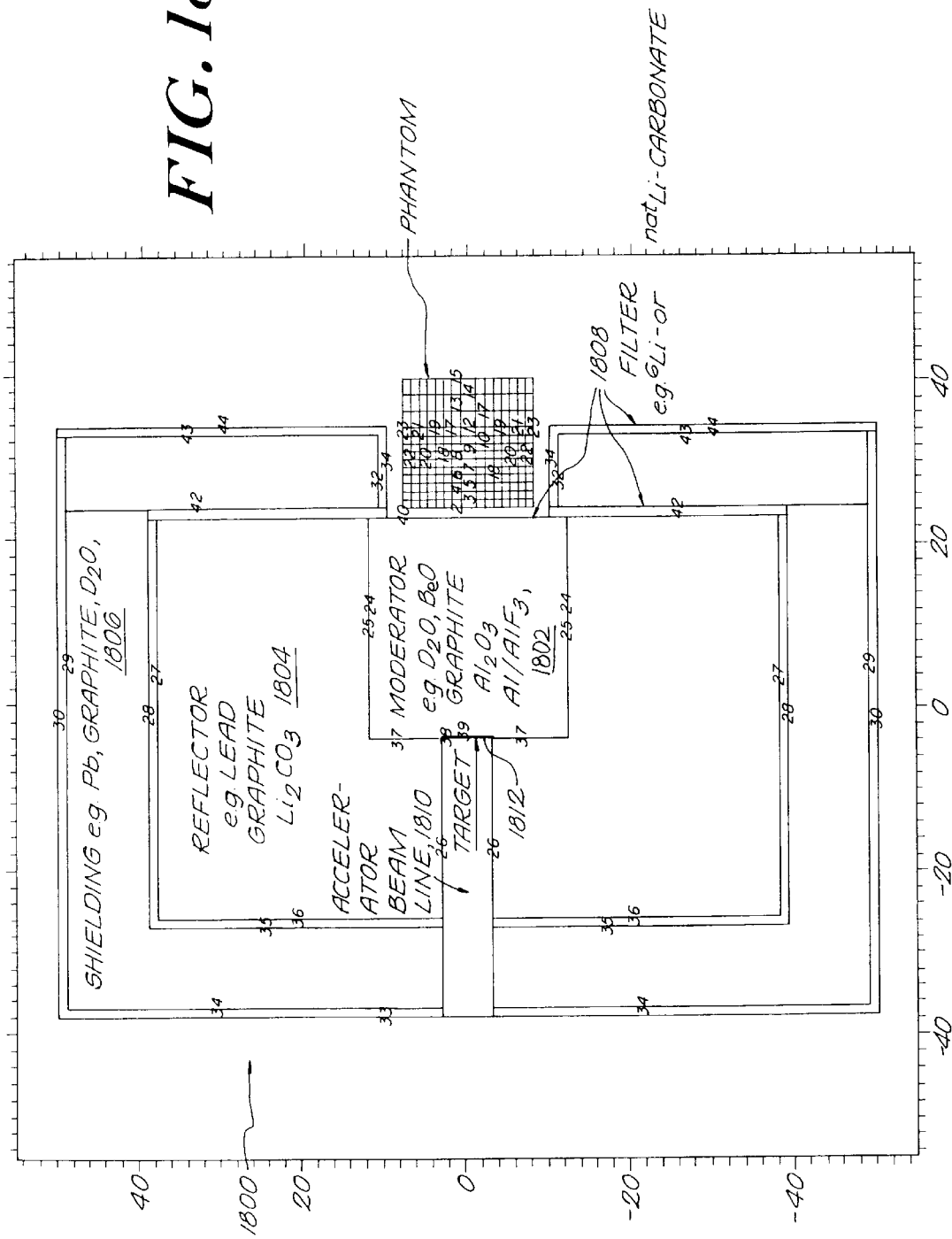
FIG. 18 is a schematic diagram of an exemplary moderator, reflector and shielding assembly.

FIG. 18 is a schematic diagram of an exemplary moderator, reflector and shielding assembly 1800 used in these simulations. The assembly includes a moderator 1802, e.g., $D_2O$, BeO, graphite, $Al_2O_3$ or $Al/AlF_3$, a reflector 1804, e.g., lead, graphite or $Li_2CO_3$, a shielding 1806, e.g., Pb, graphite or $D_2O$, a filter 1808, e.g., $^6Li$- or $^{nat}Li$-carbonate, an accelerator beam line 1810 and a target 1812.

Figure 19:
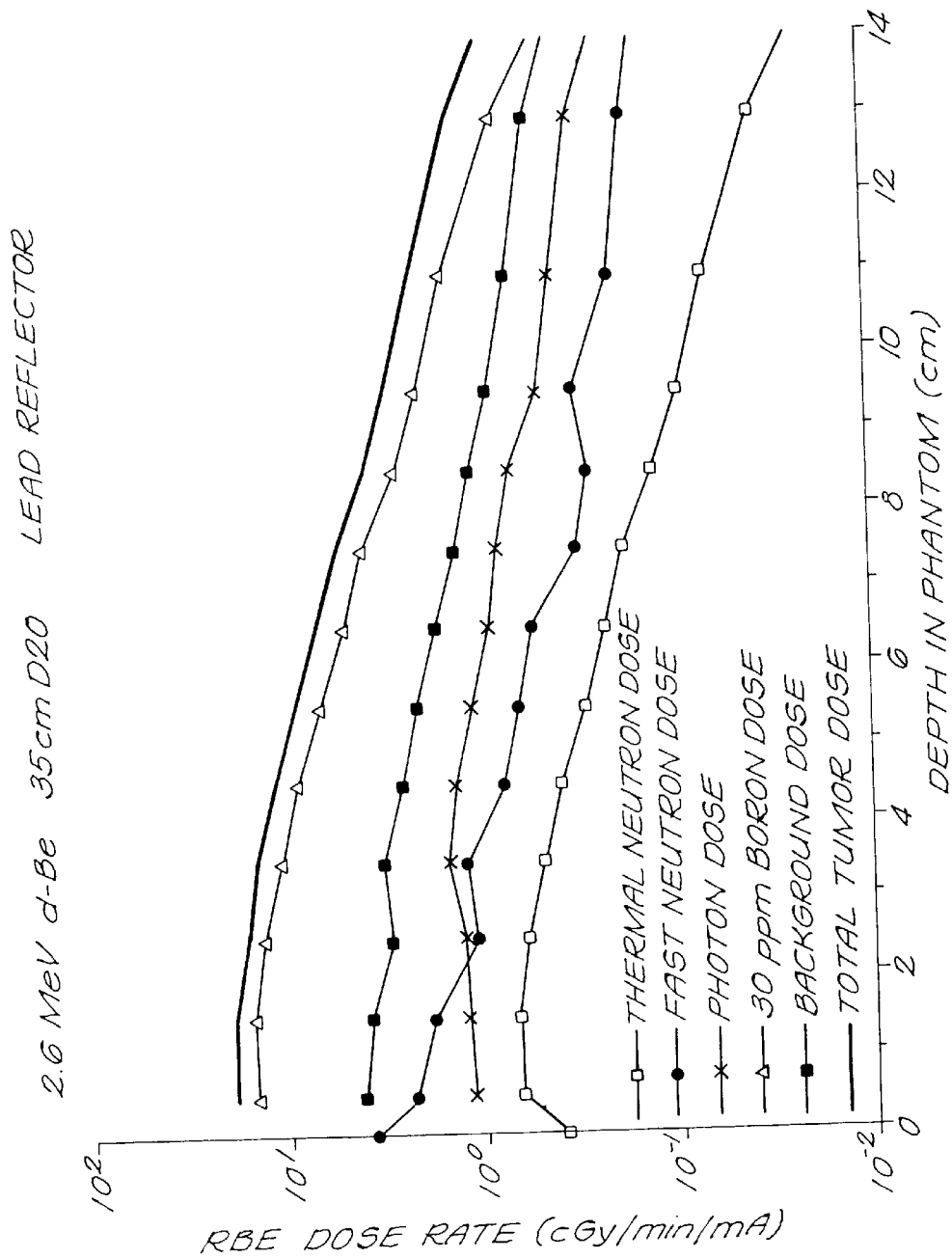
FIGS. 19, 20 and 21 are graphs which plot dose versus depth in a cylindrical brain phantom for varying moderator/reflector configurations, in which a 24 cm diameter, 35 cm long $D_2O$ moderator is used.
Figure 20:
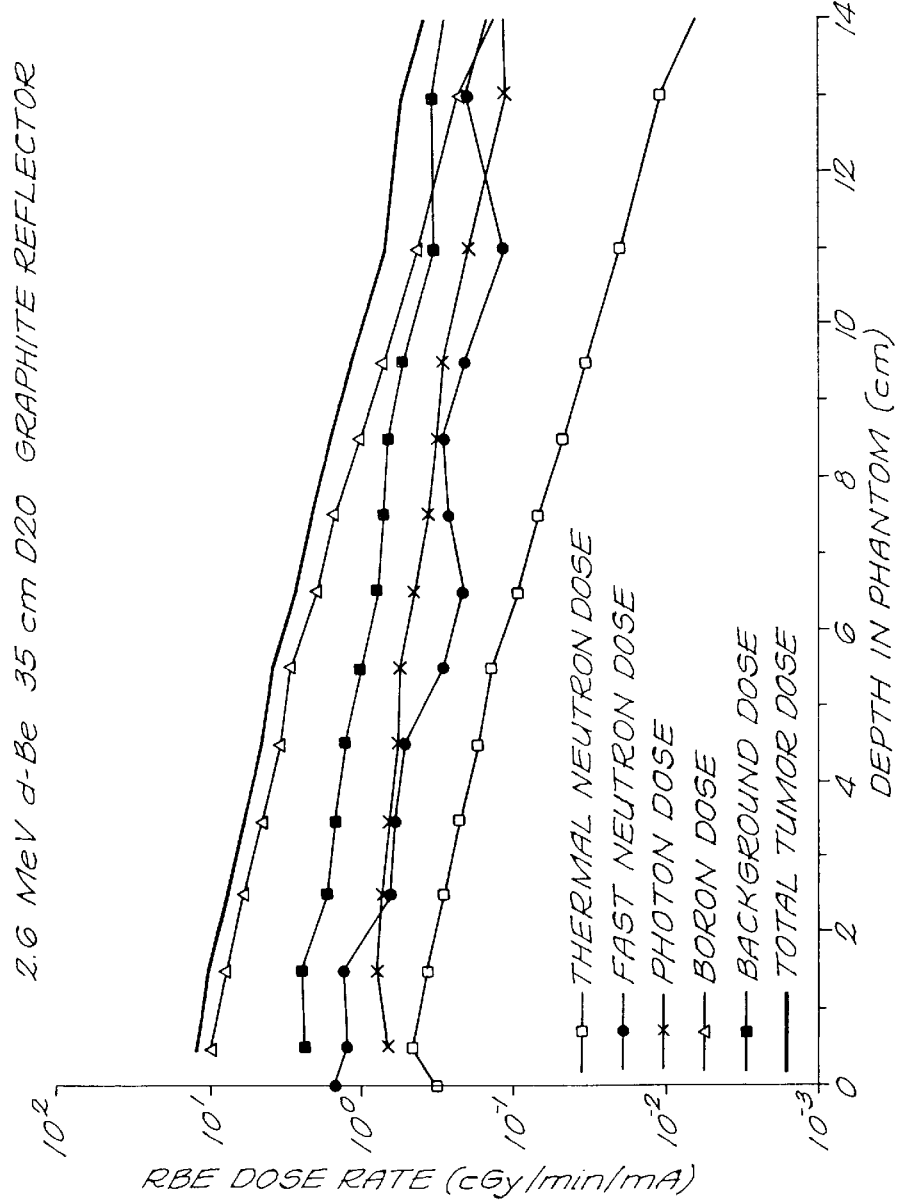
Figure 21:
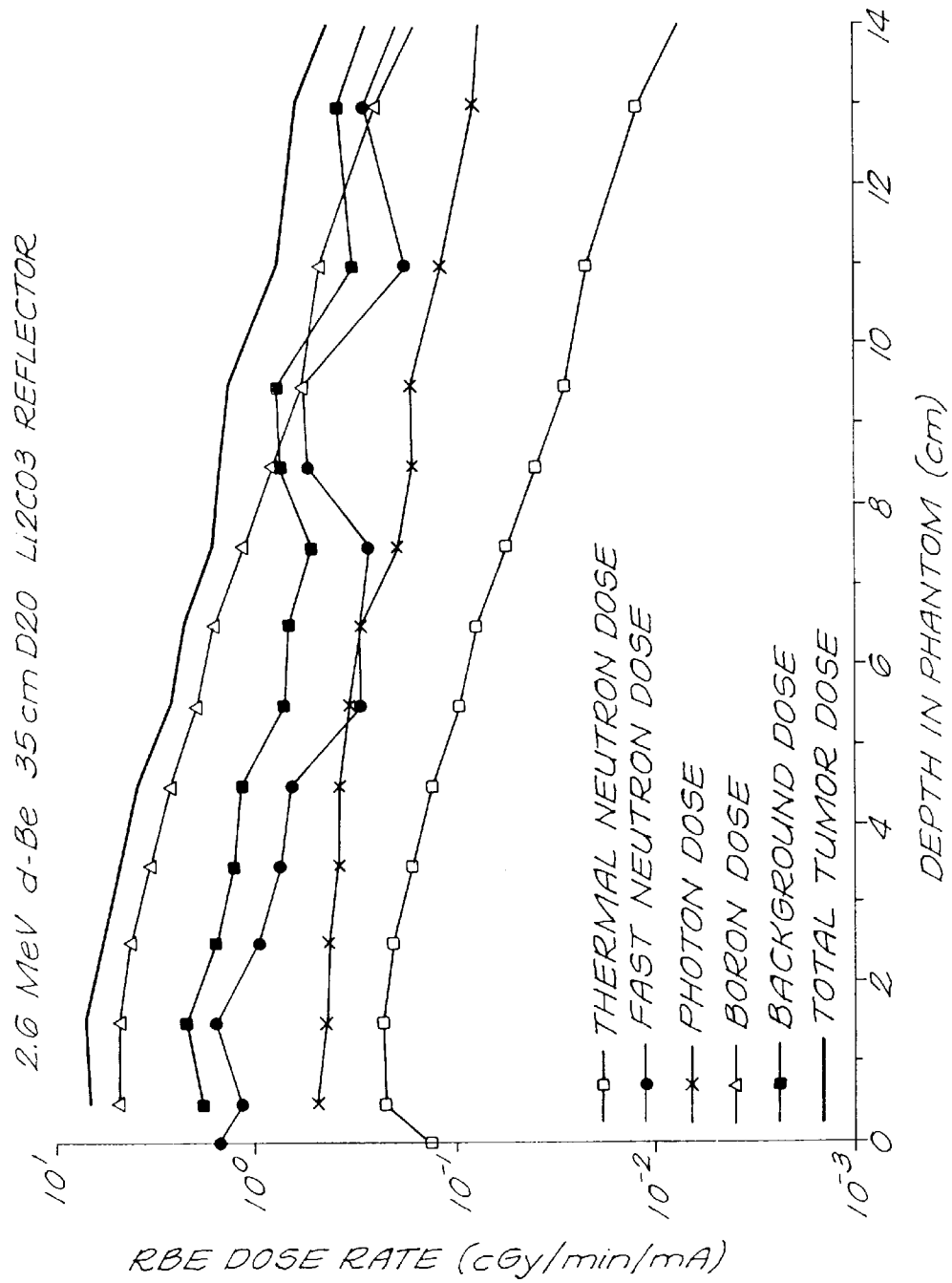

Results indicate that a number of deuteron energies and a variety of moderator/reflector configurations will produce epithermal neutron beams suitable for clinical use. Examples are shown in the graphs of FIGS. 19, 20 and 21 which plot dose versus depth in a cylindrical brain phantom for various moderator/reflector configurations. In these examples, a deuteron bombarding energy of 2.6 MeV is used, but lower energies, e.g. less than 2.0 MeV are preferable. In each example, a 24 cm diameter, 35 cm long $D_2O$ moderator is used. An 18 cm thick reflector made of lead, graphite or lithium carbonate (FIG. 4) surrounds the moderator on three sides. A thermal neutron filter such as $^6Li$- or $^{nat}Li$-carbonate removes thermal neutrons from the beam. Exemplary advantage depths and RBE dose-rates (per milliampere of deuteron current) for each beam are given in the table of FIG. 22.

Dosimetric measurements of a moderated, 2.6 MeV d-Be neutron beam were obtained in an elliptical, water-filled brain phantom. The assembly 1800 (previously designed and constructed for the use with the $^7Li$ (p,n) reaction) consists of a 24 cm diameter, 27 cm long $D_2O$ tank surrounded on three sides by an 18 cm thick lead moderator.

Dosimetry measurements were based on the protocol established by the MIT Reactor BNCT group ("Mixed field dosimetry of epithermal neutron beams for BNCT at the MIT R-II research reactor", R. Rogus et al, Med. Phys 21(10), 1994). The 14 cm elliptical brain phantom constructed by the MITR-II BNCT group was used for these measurements; dose components were assessed at depths of 1 cm and 7 cm.

The fast neutron and photon dose rates were measured using the dual ionization chamber technique. Two small ionization chambers (Far West IC-18 and IC-18G) were inserted one at a time into the water-filled head phantom. Tissue equivalent gas or $CO_2$ flowed continually through the IC-18 and IC-18G, respectively. The integrated ionization current was measured using a sensitive electrometer (Keithley 617). Ionization currents were approximately $1-3 \times 10^{-13}$ Coulomb/min.-$\mu A$. From these values, the dark currents, which were approximately $1-10 \times 10^{-15}$ Coulomb/min.-$\mu A$, were subtracted (the dark current are collected with the HV applied, but with no radiation field present). The fast neutron and photon dose components were then calculated using the calibration factors provided by the MIT Reactor BNCT Group.

The thermal neutron fluence was measured using gold activation foils. Two gold foils were taped to a plastic rod and placed at depths of 1 and 7 cm in the phantom. These foils were irradiated for approximately 45 minutes. The activities of the foils were measured using a high purity germanium detector. First the saturation activities of the foils were calculated. Then, the thermal neutron fluences were calculated assuming that the saturated activity of a cadmium covered foil to that of an uncovered foil was 0.408 (from a sample calculation of the MIT Reactor Group).

These dose components were then determined using the fluence to kerma conversion method.

Figure 23:
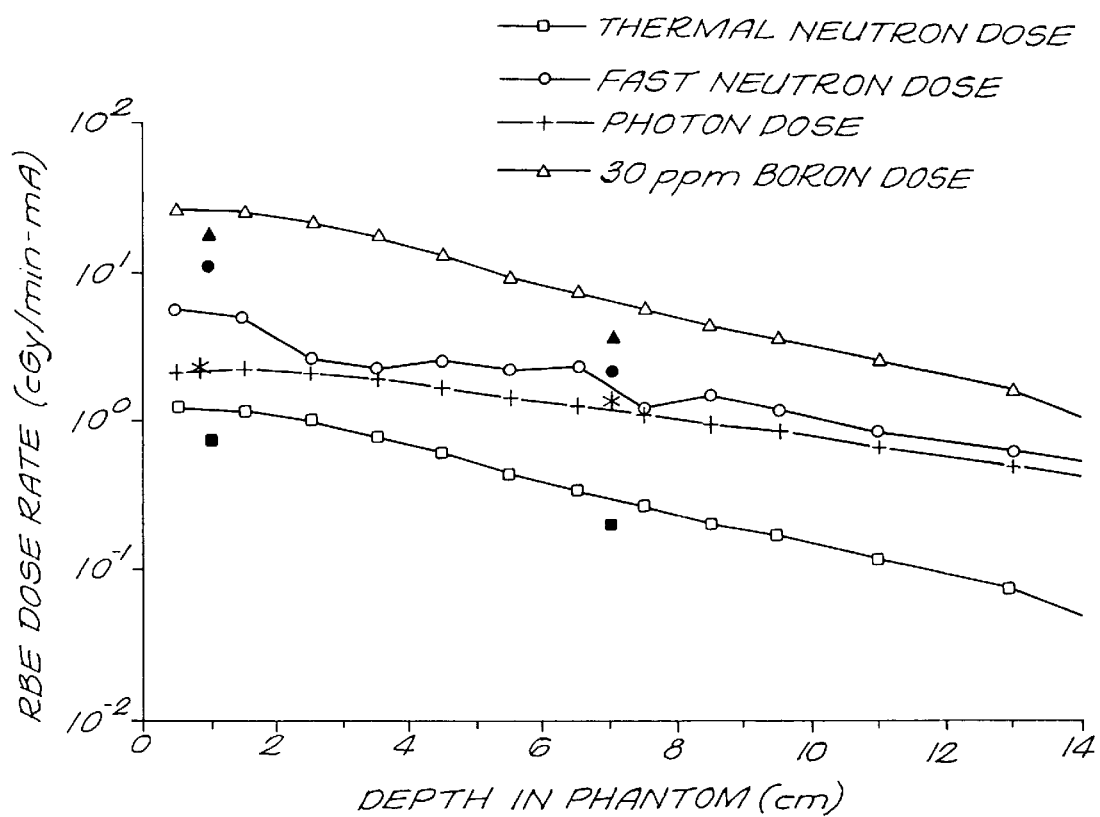
FIG. 23 is a graph showing a plot of experimentally-determined dose components compared with dosimetric data predicted by MCNP simulation.

The experimentally-determined dose components are shown on the graph of FIG. 23 and compared with dosimetric data predicted by MCNP simulation. Overall the comparison between experiment and simulation is good. At a depth of 7 cm, the measured dose components are within 30% of predictions. Nearing the surface, the measured fast neutron dose is almost a factor of two greater than predicted whereas the measured thermal dose is 30% lower than expected on the basis of simulation.

The dose rates of FIGS. 19–21 for the d-Be reaction at 2.6 MeV are competitive with the dose rates predicted using a moderated Li(p,n) beam for roughly the same energy of bombarding particle. Beryllium targets, however, offer fewer mechanical and heat removal difficulties than lithium, suggesting that the Be(d,n) reaction should be actively considered for implementation of neutron capture therapies. Results also indicate that therapeutically useful neutron beams can be produced using the higher bombarding energies (>6 MeV) generated by biomedical cyclotrons.

The foregoing description has been set forth to illustrate the invention and is not intended to be limiting. Since modifications of the described embodiments incorporating the spirit and substance of the invention may occur to persons skilled in the art, the scope of the invention should be limited solely with reference to the appended claims and equivalents thereof.

What is claimed is:

1. A method of treating diseased tissue of a human joint, comprising:

providing a beam of energetic neutrons;

shifting an energy spectrum of said beam such that the energy of said beam are reduced to relatively low energy;

incorporating a nuclide having a high neutron capture cross-section in proximity of said diseased tissue; and applying said spectrum shifted, low energy beam in one or more directions to the diseased tissue of said human joint, wherein said spectrum shifted, low energy beam interacts with said nuclide such that energetic particles or photons are created which damage said diseased tissue.

2. A method of treating diseased tissue, comprising:

generating a neutron beam by a charged particle reaction in which deuterons are the bombarding particles of a selected target and the bombarding deuterons have energies of less than 2.0 MeV;

shifting an energy spectrum of said beam such that the energy of said beam is reduced to a substantially epithermal energy spectrum;

incorporating a nuclide having a high neutron capture cross-section in proximity of said diseased tissue; and applying said spectrum shifted, low energy beam in one or more directions to the diseased tissue, wherein said spectrum shifted, low energy beam interacts with said nuclide such that energetic particles or photons are created which damage said diseased tissue.

3. A system for treating diseased tissue of a human joint, said joint having introduced thereto a nuclide having a high neutron capture cross-section incorporated in the proximity of said diseased tissue, said system comprising:

a beam source which generates a beam of energetic neutrons;

a moderator which shifts an energy spectrum of said beam such that the energy of said beam is reduced to relatively low energy so as to provide a spectrum shifted, low energy beam; and an applicator which applies said spectrum shifted, low energy beam in one or more directions to the diseased tissue of said human joint, wherein said spectrum shifted, low energy beam interacts with said nuclide such that energetic particles or photons are created which damage said diseased tissue.

4. A system of treating diseased tissue, said diseased tissue having introduced thereto a nuclide with a high neutron capture cross-section in the proximity thereof, said system comprising:

a beam source which generates a neutron beam by a charged particle reaction in which deuterons are the bombarding particles of a selected target and the bombarding deuterons have energies of less than 2.0 MeV;

a moderator which shifts an energy spectrum of said beam such that the energy of said beam is reduced to a substantially epithermal energy spectrum so as to provide a spectrum shifted, low energy beam; and an applicator which applies said spectrum shifted, low energy beam in one or more directions to the diseased tissue, wherein said spectrum shifted, low energy beam interacts with said nuclide such that energetic particles or photons are created which damage said diseased tissue.

5. An apparatus for generating a beam of low energy neutrons for irradiation of a human joint, said apparatus comprising:

a source which produces energetic neutrons;

a moderator which shifts an energy spectrum of said energetic neutrons to lower energies so as to provide a spectrum shifted, low energy beam, wherein said spectrum shifted neutrons define a beam resulting in a therapeutic ratio of 4 or greater upon interacting with said joint and an exogenous nuclide having a high neutron capture cross-section contained within said human joint.

6. An apparatus for generating a beam of low energy neutrons for irradiation of diseased tissue, said apparatus comprising:

a source which generates energetic neutrons by a charged particle reaction in which deuterons are the bombarding particles of a selected target and the bombarding deuterons have energies of less than 2.0 MeV;

a moderator which shifts an energy spectrum of said energetic neutrons such that the energies of said neutrons are reduced to a substantially epithermal energy spectrum, wherein said spectrum shifted neutrons define a low energy beam which interacts with an exogenous nuclide having a high neutron capture cross-section contained within said diseased tissue such that energetic particles or photons are created which damage said diseased tissue.

* * * * *